(12) United States Patent
Kono

(10) Patent No.: US 10,520,362 B2
(45) Date of Patent: Dec. 31, 2019

(54) SPECTROSCOPIC MEASUREMENT DEVICE AND SPECTROMETRY SYSTEM

(71) Applicant: HAMAMATSU PHOTONICS K.K., Hamamatsu-shi, Shizuoka (JP)

(72) Inventor: Makoto Kono, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 16/347,270

(22) PCT Filed: Nov. 13, 2017

(86) PCT No.: PCT/JP2017/040743
§ 371 (c)(1),
(2) Date: May 3, 2019

(87) PCT Pub. No.: WO2018/088553
PCT Pub. Date: May 17, 2018

(65) Prior Publication Data
US 2019/0277697 A1 Sep. 12, 2019

(30) Foreign Application Priority Data
Nov. 14, 2016 (JP) .................... 2016-221594

(51) Int. Cl.
*G01J 3/28* (2006.01)
*G01J 3/42* (2006.01)
(Continued)

(52) U.S. Cl.
CPC .............. *G01J 3/42* (2013.01); *G01J 3/0256* (2013.01); *G01J 3/0262* (2013.01); *G01N 21/01* (2013.01); *G01N 21/27* (2013.01)

(58) Field of Classification Search
CPC .......... G01J 3/42; G01J 3/0256; G01J 3/0262; G01J 3/02; G01N 21/27; G01N 21/01
See application file for complete search history.

(56) References Cited

U.S. PATENT DOCUMENTS 5,548,677 A * 8/1996 Kakii ..................... G02B 6/262
385/92

FOREIGN PATENT DOCUMENTS

| JP | S54-110886 A | 8/1979 |
| JP | H03-25348 A | 2/1991 |

(Continued)

OTHER PUBLICATIONS

International Preliminary Report on Patentability dated May 23, 2019 for PCT/JP2017/040743.

*Primary Examiner* — Abdullahi Nur
(74) *Attorney, Agent, or Firm* — Drinker Biddle & Reath LLP

(57) ABSTRACT

A spectroscopic measurement device emits light to a measurement target and measures the measurement light output from the measurement target in accordance with the light emission. A spectroscopic measurement device includes: a first housing having a light shielding property and configured to house a light source that emits light and having a first opening through which the light emitted from the light source passes; a second housing having a light shielding property and having a second opening through which the measurement light passes and configured to house a spectrometer that receives the measurement light that has passed through the second opening; and a junction configured to join the first housing and the second housing such that relative positions of the first housing and the second housing can be changed.

15 Claims, 18 Drawing Sheets

(51) Int. Cl.
*G01J 3/02* (2006.01)
*G01N 21/01* (2006.01)
*G01N 21/27* (2006.01)

(56) References Cited

FOREIGN PATENT DOCUMENTS

| | | |
|---|---|---|
| JP | H07-198597 A | 8/1995 |
| JP | 2003-510560 A | 3/2003 |
| JP | 3446120 B2 | 9/2003 |
| JP | 2014-102217 A | 6/2014 |
| WO | WO-01/06232 A2 | 1/2001 |

* cited by examiner

SPECTROSCOPIC MEASUREMENT DEVICE AND SPECTROMETRY SYSTEM

TECHNICAL FIELD

One aspect of the present invention relates to a spectroscopic measurement device and a spectrometry system.

BACKGROUND ART

An apparatus described in Patent Literature 1 is known as an example of a conventional spectroscopic measurement device. The apparatus described in Patent Literature 1 uses a light source lamp (light source) to emit light onto a specimen (measurement target) mounted on a specimen table, and detects the light (measurement light) output from the specimen corresponding to the light emission by using an integrating sphere and a photodetector (spectrometer), so as to measure optical properties of the specimen.

CITATION LIST

Patent Literatures

Patent Literature 1: Japanese Patent No. 3446120

SUMMARY OF INVENTION

Technical Problem

Meanwhile, relative positions at which the light source and the spectrometer should be disposed are different between the case of measuring transmitted light, that is, light transmitted through the measurement target, and the case of measuring reflected light, that is, light reflected by the measurement target. Accordingly, the spectroscopic measurement device described above includes: a motor-rotatable first rotating member constituting an optical path of the light emitted onto the measurement target; and a motor-rotatable second rotating member constituting an optical path of the measurement light output from the measurement target, in order to arrange the light source and the spectrometer at desired relative positions. This, however, would complicate the configuration and enlarge the apparatus. In an attempt, in particular, to shield external light that is likely to greatly influence the measurement of the optical properties of the measurement target, for example, it would be necessary to dispose the whole device in a housing having a light shielding property, and this would further enlarge the device.

In view of the above, one aspect of the present invention is to provide a spectroscopic measurement device capable of disposing a light source and a spectrometer at desired relative positions and downsizing the device, and provide a spectrometry system including the spectroscopic measurement device.

Solution to Problem

A spectroscopic measurement device according to one aspect of the present invention is a spectroscopic measurement device configured to emit light onto a measurement target to measure measurement light output from the measurement target corresponding to the light emission, the device including: a first housing having a light shielding property and configured to house a light source that emits light and having a first opening through which the light emitted from the light source passes; a second housing having a light shielding property and having a second opening through which the measurement light passes and configured to house a spectrometer that receives the measurement light that has passed through the second opening; and a junction configured to join the first housing and the second housing such that relative positions of the first housing and the second housing can be changed.

The spectroscopic measurement device enables, with its junction, the first housing and the second housing to be positioned in a desired positional relationship, and consequently enables the light source housed in the first housing and the spectrometer housed in the second housing to be disposed at desired relative positions with a simple configuration. Additionally, the first housing and the second housing have a light shielding property, and thus, can shield external light without a need to provide a separate configuration. Accordingly, it is possible to arrange the light source and the spectrometer at desired relative positions and downsize the apparatus.

In the spectroscopic measurement device, the junction may relatively rotatably join the first housing and the second housing. In this case, by relatively rotating, by the junction, the first housing that houses the light source and the second housing that houses the spectrometer, it is possible to arrange the light source and the spectrometer at desired relative angular positions.

In the spectroscopic measurement device according to one aspect of the present invention, the junction may slidably join one of the first housing and the second housing to the other in a direction to allow the first opening and the second opening to come closer to or away from each other. In this case, the measurement target can be firmly sandwiched and held by the first opening and the second opening regardless of the thickness of the measurement target.

In the spectroscopic measurement device according to one aspect of the present invention, the junction may be capable of changing the relative positions to a position at which the first opening and the second opening face each other. In this case, the transmitted light, that is, light transmitted through the measurement target, can be received by the spectrometer as measurement light.

In the spectroscopic measurement device according to one aspect of the present invention, the junction may be configured to be able to change the relative position to a position at which an optical axis of the light to be emitted onto the measurement target and an optical axis of the measurement light output from the measurement target intersect at a predetermined angle. In this case, reflected light reflected by the measurement target can be received by the spectrometer as measurement light.

The spectroscopic measurement device according to one aspect of the present invention may further include an attachment to detachably hold the first housing and the second housing joined by the junction. In this case, the first housing and the second housing positioned in a desired positional relationship by the junction can be held by the attachment.

In the spectroscopic measurement device according to one aspect of the present invention, the attachment may have a light shielding property, and may internally include: a first optical path being an optical path of the light emitted onto the measurement target and is continuous with the first opening; and a second optical path being an optical path of the measurement light output from the measurement target and is continuous with the second opening. The configuration, in this case, would suppress invasion of external light into the first optical path and the second optical path provided inside the attachment.

In the spectroscopic measurement device according to one aspect of the present invention, the attachment may have a position regulator to regulate a position of the measurement target or a position of a container accommodating the measurement target. In this case, it is possible to hold the measurement target or the container accommodating the measurement target by the position regulator.

A spectrometry system according to one aspect of the present invention includes: the above-described spectroscopic measurement device; a measurement result transmission unit provided in the spectroscopic measurement device and configured to transmit a measurement result of the spectrometer; and a measurement result processing device configured to receive the measurement result of the spectrometer from the measurement result transmission unit directly or through a network and perform processing of the measurement result.

Since this spectrometry system includes the above-described spectroscopic measurement device, it is possible to obtain the above effect of enabling the light source and the spectrometer to be disposed at desired relative positions and enabling downsizing of the device. Furthermore, it is possible to have a configuration in which the spectroscopic measurement device has no measurement result processing function, leading to downsizing of the spectroscopic measurement device.

The spectrometry system according to one aspect of the present invention further includes: a control terminal configured to generate a control signal for controlling the light source in accordance with operation of an operator and transmit the control signal; a control signal reception unit provided in the spectroscopic measurement device and configured to receive the control signal from the control terminal directly or through a network; and a light source control unit provided in the spectroscopic measurement device and configured to control the light source on the basis of the control signal received by the control signal reception unit. With this configuration, it is possible to remotely operate the light source.

Advantageous Effects of Invention

According to one aspect of the present invention, it is possible to provide a spectroscopic measurement device capable of disposing the light source and the spectrometer at desired relative positions and downsizing the device, and a spectrometry system including the spectroscopic measurement device.

DESCRIPTION OF EMBODIMENTS

Figure 1:
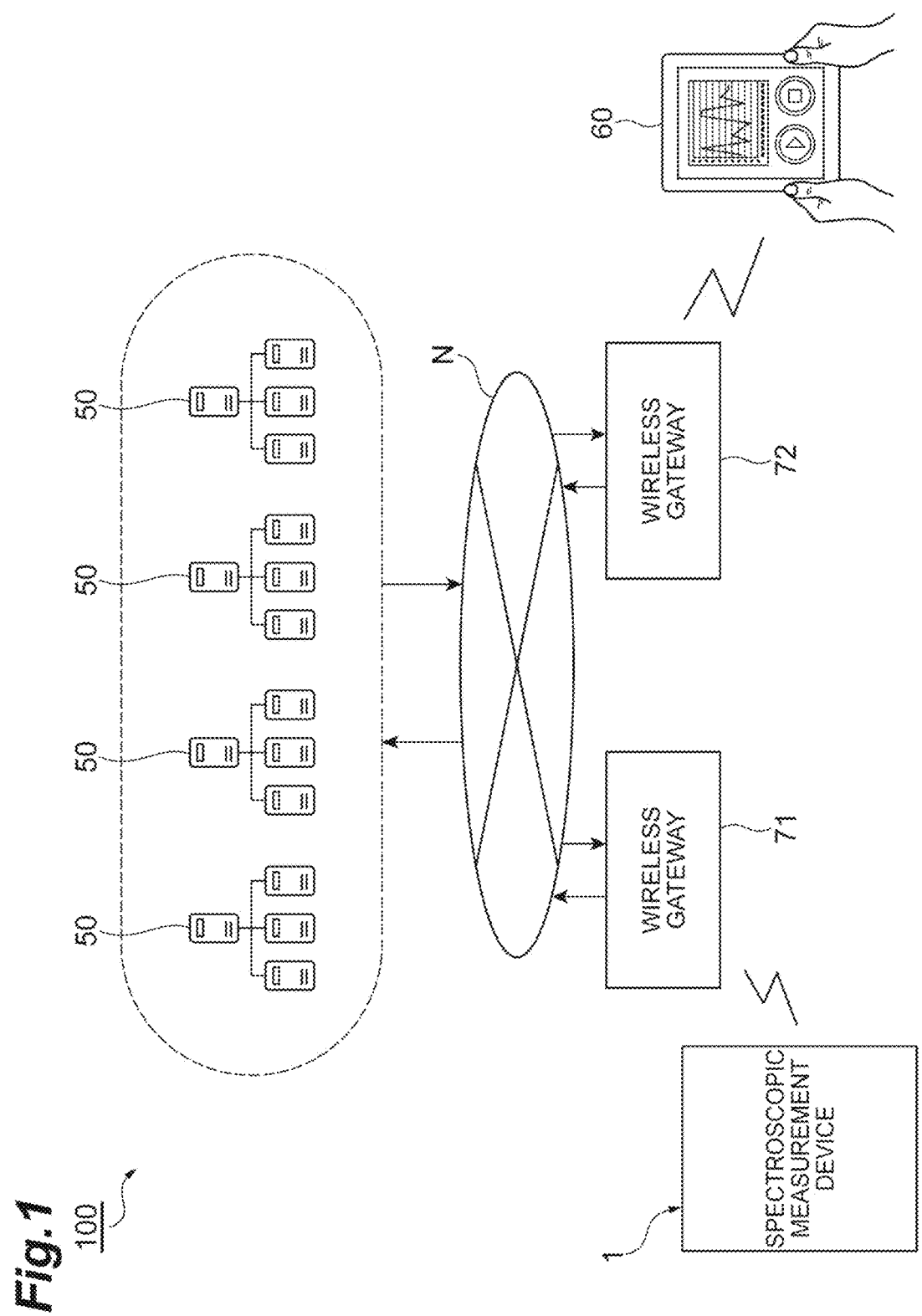
FIG. 1 is a configuration diagram illustrating a spectrometry system according to a first embodiment.

Hereinafter, one embodiment of the present invention will be described in detail with reference to the accompanying drawings. In the following, the same or equivalent elements are denoted by the same reference numerals, and duplicate explanation is omitted.

First Embodiment

As illustrated in FIG. 1, a spectrometry system 100 according to a first embodiment includes: a spectroscopic measurement device 1; a data processing server 50; and a mobile information terminal 60. The spectrometry system 100 has a configuration in which the spectroscopic measurement device 1, the data processing server 50, and the mobile information terminal 60 can perform data communication with each other via a network N.

First, a configuration of the spectroscopic measurement device 1 will be described. As illustrated in FIGS. 2 to 5, the spectroscopic measurement device 1 is a mobile-type (portable-type) measurement device that emits light to a measurement target S and measures measurement light output from the measurement target S corresponding to the light emission. The spectroscopic measurement device 1 according to the present embodiment, in particular, can perform transmitted light measurement using transmitted light, that is, light transmitted through the measurement target S, as measurement light. The spectroscopic measurement device 1 includes a first housing 10, a second housing 20, and a junction 30. In the spectroscopic measurement device 1, the first housing 10 and the second housing 20 are joined by the junction 30.

Figure 3:
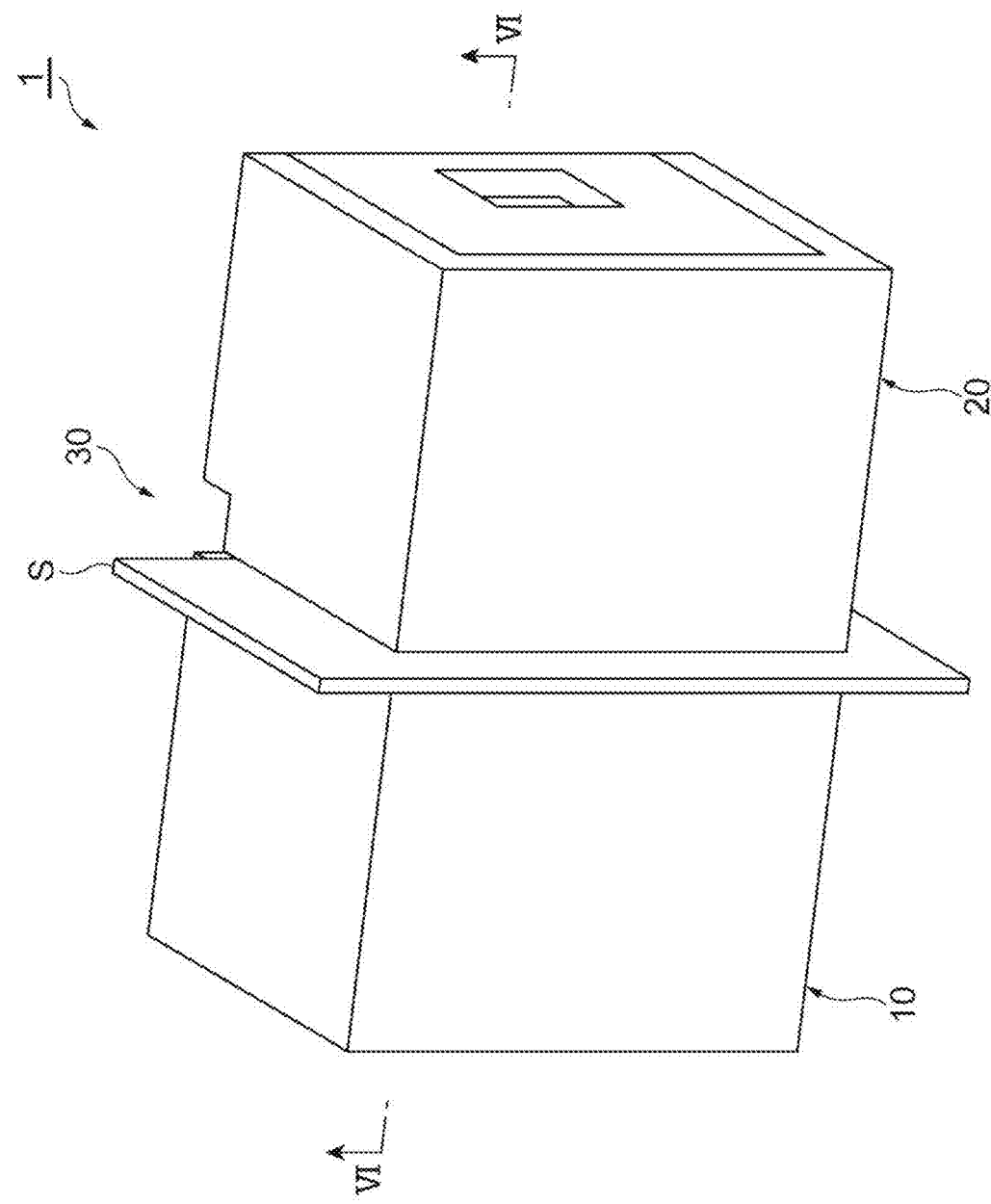
FIG. 3 is a perspective view illustrating a state of measuring the measurement light in the spectroscopic measurement device of FIG. 2.
Figure 4:
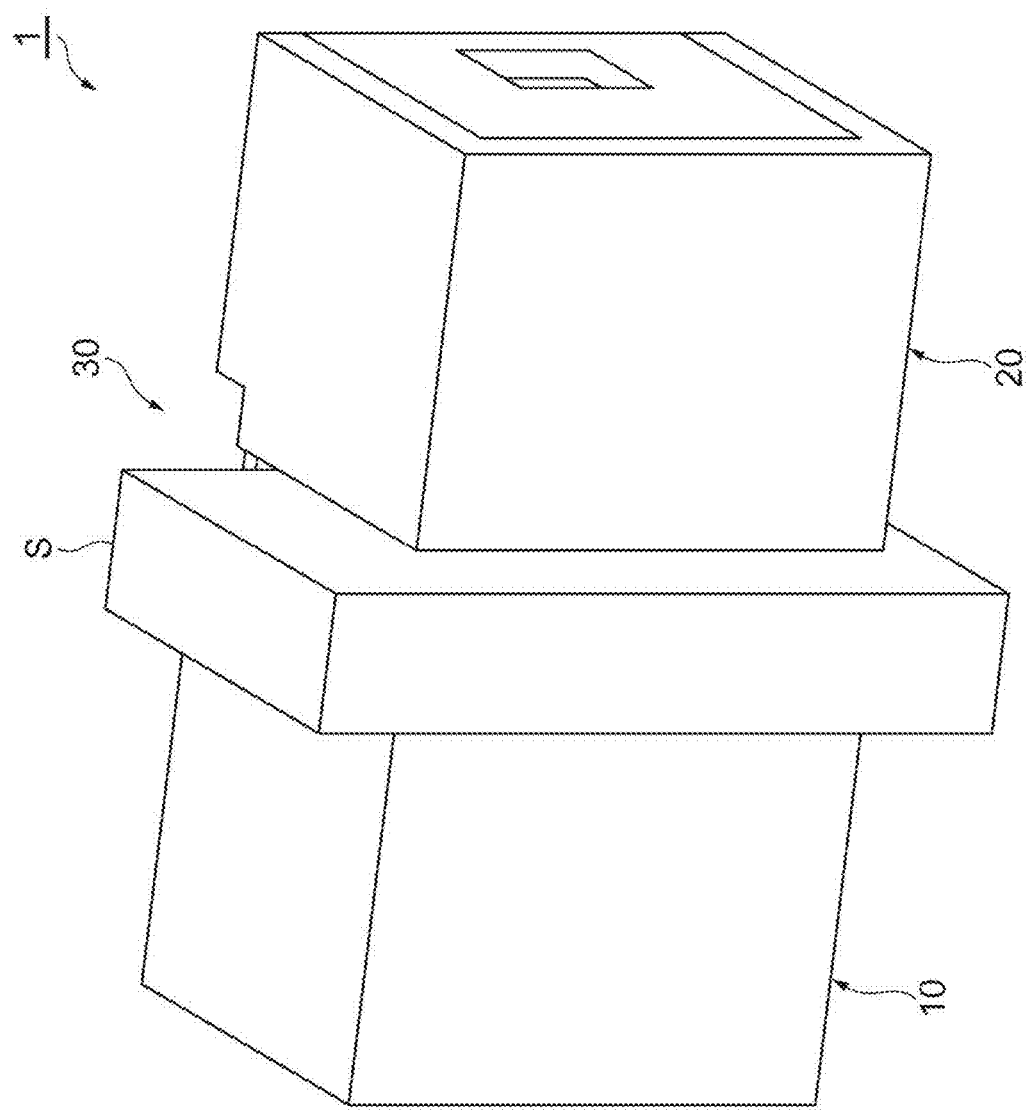
FIG. 4 is a perspective view illustrating a state where measurement light is measured by the spectroscopic measurement device of FIG. 2.

An example of the measurement target S is a plant, although not particularly limited. The measurement target S is also referred to as a sample or a specimen. The measurement target S may also be a substance in a form of liquid, powder, or gas, stored in a container, for example, in addition to a solid substance. The thickness of the measurement target S is not particularly limited, and the measurement target S may be thin, for example, as illustrated in FIG. 3, or it may be thick as illustrated in FIG. 4.

Figure 5:
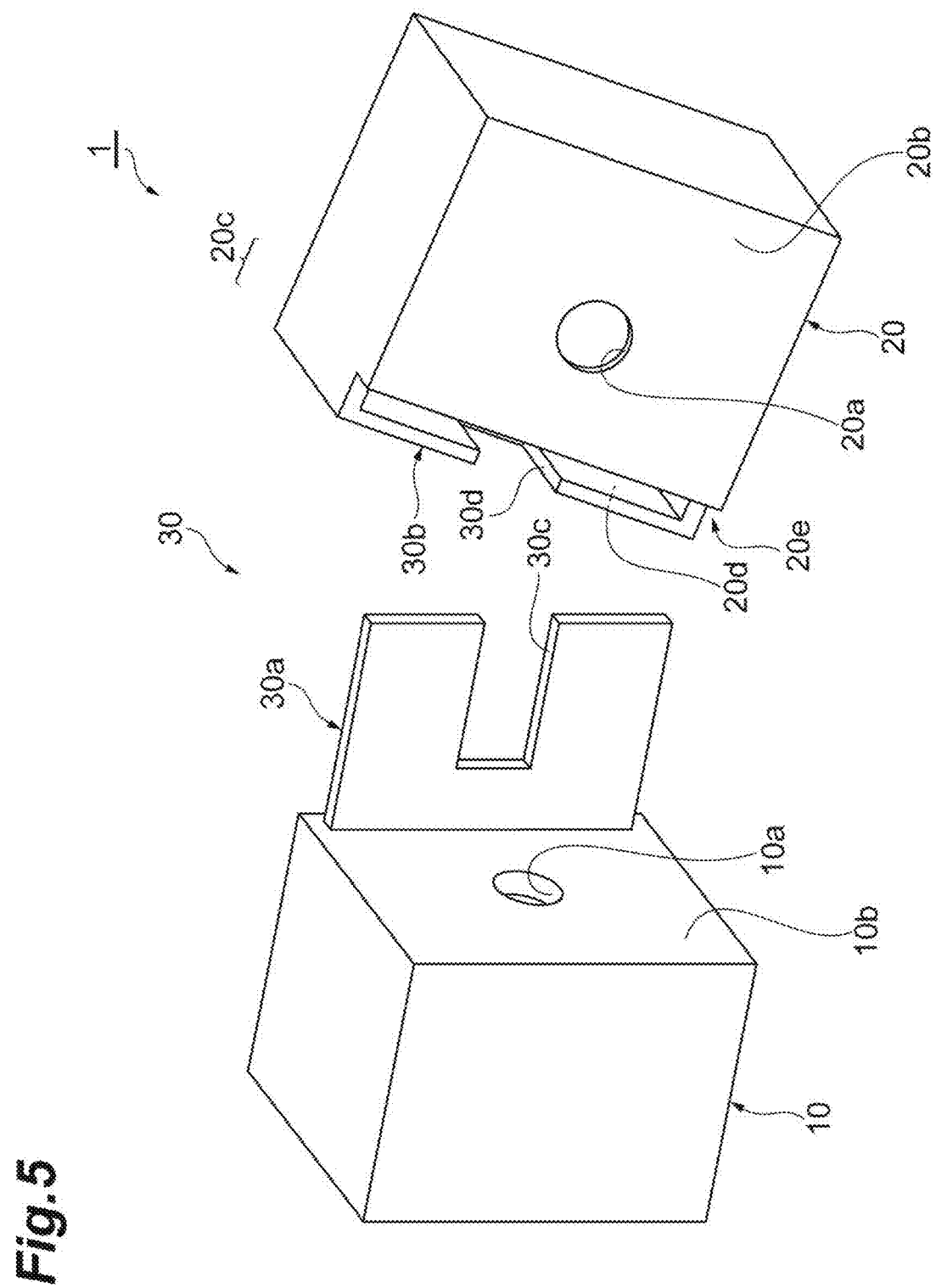
FIG. 5 is a perspective view illustrating a state where the spectroscopic measurement device of FIG. 2 is disassembled.
Figure 6:
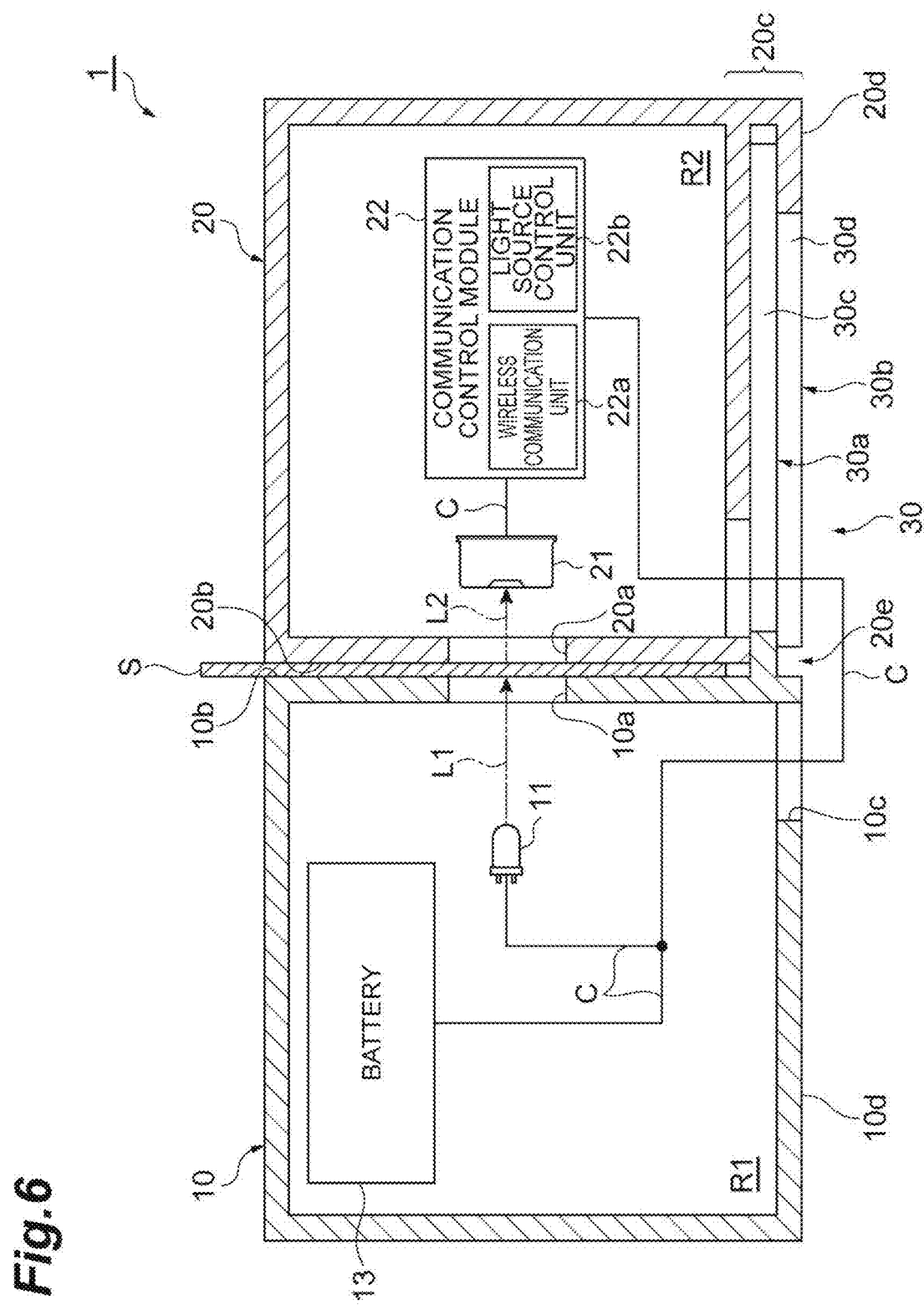
FIG. 6 is a diagram schematically illustrating a cross section taken along line VI-VI of FIG. 3.

As illustrated in FIGS. 5 and 6, the first housing 10 is a box member having a rectangular parallelepiped outer shape and having an internal space R1. The first housing 10 is a light projection block for projecting light L1 onto the measurement target S. The first housing 10 accommodates a light source 11 and a battery 13 in the internal space R1. The battery 13 supplies electric power to the light source 11 and to a spectrometer 21 and a communication control module 22 of the second housing to be described below.

The light source 11 emits the light L1. Examples of the light source 11 include a light emitting diode or a mini lamp (incandescent light bulb). The light source 11 is provided so as to be changeable in the first housing 10. Specifically, wavelength characteristics of the light L1 of the light source 11 are changeable in accordance with the measurement application. For example, when a light emitting diode in the ultraviolet range is used as the light source 11, it is possible to measure the fluorescence of the measurement target S. For example, when a white light emitting diode is used as the light source 11, it is possible to measure the chromaticity of the measurement target S. In addition, when a light emitting diode is used as the light source 11, it is possible to turn on and off the light source 11 in a short cycle with pulse lighting.

One side surface 10b of the first housing 10 has a first opening 10a through which the light L1 emitted from the light source 11 passes. The first opening 10a having a circular cross section is provided on an optical axis of the light L1 from the light source 11 through an outer wall of the first housing 10. The first opening 10a is closed with a transparent member (such as an acrylic plate) that transmits the light L1. This makes it possible to prevent the measurement target S from directly coming in contact with the light source 11. Note that a lens may be disposed in the first opening 10a so as to facilitate enhancement of the ability to collect the light L1. The first housing 10 has a light shielding property. Here, the first housing 10 is formed of resin having high light shielding property so as not to obstruct wireless communication by a wireless communication unit 22a to be described below.

The second housing 20 is box member having a rectangular parallelepiped outer shape and having an internal space R2. The second housing 20 is a light receiving block for receiving measurement light L2 from the measurement target S. The second housing 20 accommodates the spectrometer 21 and the communication control module 22 in the internal space R2.

The spectrometer 21 receives the measurement light L2, and analyzes the measurement light L2 separately for individual wavelengths. Examples of the spectrometer 21 applicable include a micro-spectrometer or a micro-spectroscopic sensor.

The communication control module 22 includes a central processing unit (CPU). The communication control module 22 includes: a wireless communication circuit configured to implement a wireless communication function with the outside; and a driver circuit configured to implement a control function of the light source 11. The communication control module 22 is electrically connected to the spectrometer 21, and to the light source 11 and the battery 13 provided in the first housing 10, via a cable C such as a flexible cable having flexibility or elasticity. Meanwhile, another side surface 10d adjacent to the one side surface 10b of the first housing 10 has a third opening 10c communicating with the internal space R1. The cable C can be pulled out from the inside of the first housing 10 to the outside via the third opening 10c.

The communication control module 22 functionally includes a wireless communication unit (measurement result transmission unit, control signal reception unit) 22a, and a light source control unit 22b. The wireless communication unit 22a receives a control signal (also referred to as a control command) for controlling the light source 11 from the outside by wireless communication and also transmits a signal related to the measurement result of the spectrometer 21 to the outside by wireless communication. The light source control unit 22b performs control (ON/OFF control, etc.) of the light source 11 on the basis of the control signal received by the wireless communication unit 22a.

One side surface 20b of the second housing 20 has a second opening 20a through which the measurement light L2 passes. The spectrometer 21 is disposed at a position in proximity to the second opening 20a in the internal space R2 in a state where an entrance slit of the spectrometer 21 faces the second opening 20a. The second opening 20a is closed with a transparent member (such as an acrylic plate) that transmits the measurement light L2. This makes it possible to prevent the measurement target S from directly coming in contact with the spectrometer 21. Note that a lens may be disposed in the second opening 20a so as to facilitate enhancement of the ability to collect the measurement light L2. The second housing 20 has a light shielding property. Here, the second housing 20 is formed of resin having high light shielding property so as not to obstruct wireless communication by a wireless communication unit 22a.

Figure 2:
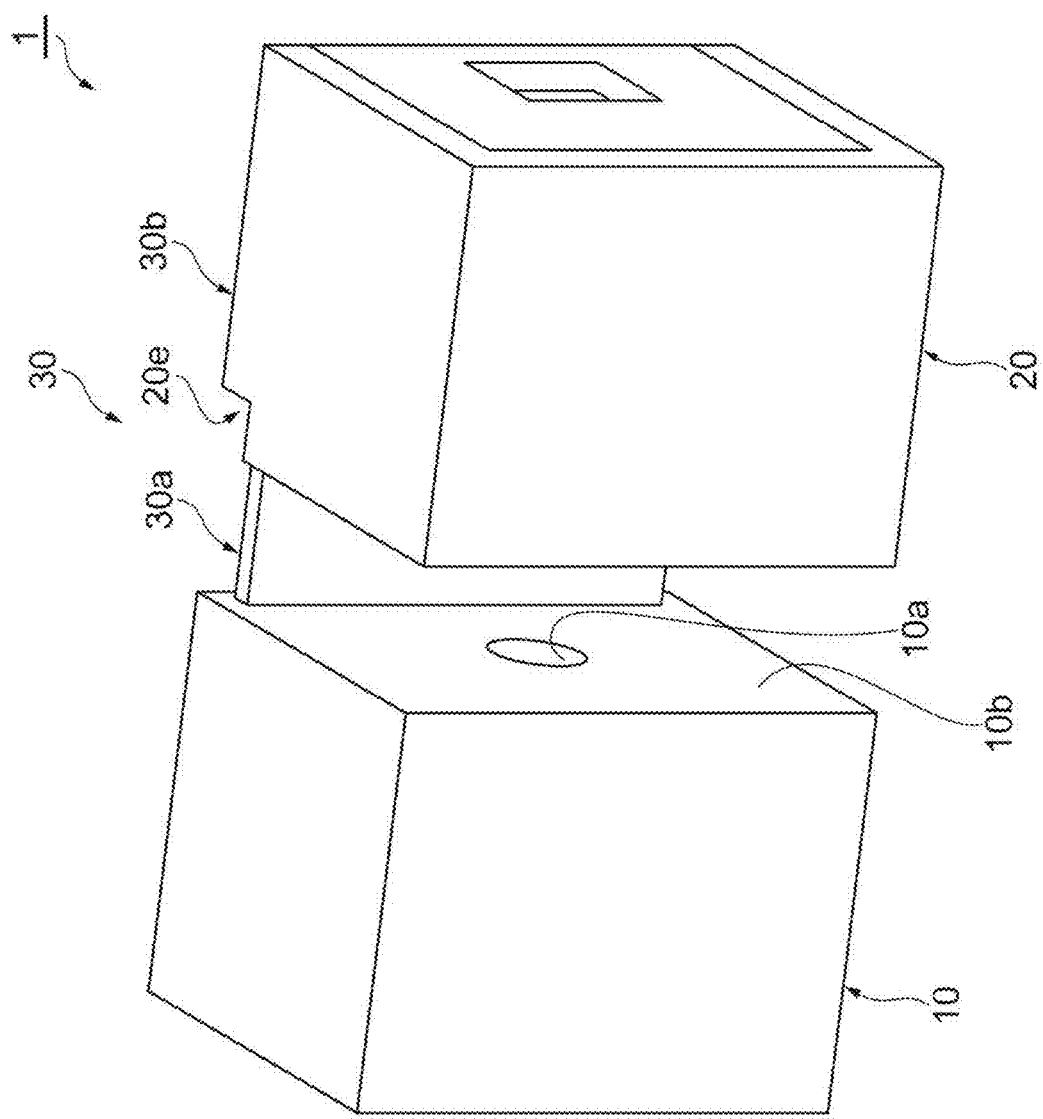
FIG. 2 is a perspective view illustrating a spectroscopic measurement device of FIG. 1.

As illustrated in FIGS. 2, 5, and 6, the junction 30 joins the first housing 10 and the second housing 20 such that the relative positions of the first housing 10 and the second housing 20 are changeable. Specifically, the junction 30 slidably joins the second housing 20 to the first housing 10 in a direction to allow the first opening 10a and the second opening 20a to come close to or away from each other, in a state where the first opening 10a and the second opening 20a face each other. With this configuration, the junction 30 enables the light source 11 of the first housing 10 and the spectrometer 21 of the second housing 20 to be disposed at desired relative positions. The desired relative position in the present embodiment is a position where the optical axis of the light L1 to be emitted onto the measurement target S and the optical axis of the measurement light L2 output from the measurement target S are coaxial, being a position at which the first housing 10 and the second housing 20 are in contact with the measurement target S.

The junction 30 is a sliding mechanism that slidably joins the second housing 20 to the first housing 10. The junction 30 includes an inserting part 30a and an insert receiving part 30b. The inserting part 30a is provided upright on one side surface 10b of the first housing 10. Specifically, the inserting part 30a is provided so as to protrude in a rectangular flat plate shape in a direction orthogonal to the one side surface 10b at an edge portion along one side of the one side surface 10b. The inserting part 30a has a rectangular cutout 30c formed to open to the distal end side and having a rectangular shape when viewed in a thickness direction of the inserting part 30a. The cutout 30c is provided in a central portion of the inserting part 30a in the direction along the one side of the one side surface 10b.

The insert receiving part 30b is a recess (hole) formed along one side on an adjacent other side surface 20d on the one side surface 20b of the second housing 20. The insert receiving part 30b is formed in a rectangular cross section corresponding to the shape of the inserting part 30a, on the side wall portion 20c on the other side surface 20d side of the second housing 20. The insert receiving part 30b is provided on a bottom surface of a stepped portion 20e formed by cutting out an edge portion along the one side of the one side surface 20b.

The insert receiving part 30b communicates with a cutout 30d formed in the side wall portion 20c. The cutout 30d opens on the bottom surface of the stepped portion 20e and is formed in a rectangular shape when it is viewed from the other side surface 20d. The cutout 30d is provided in a central portion of the other side surface 20d in the direction along the one side of the one side surface 20b. As will be described below, the cutout 30d is formed at a position corresponding to the position of the cutout 30c of the inserting part 30a in a state where the inserting part 30a is inserted in the insert receiving part 30b. The cable C can be pulled out from the inside of the second housing 20 to the outside via the cutouts 30c and 30d (refer to FIG. 6).

In the above configuration, the junction 30 is in a state where the inserting part 30a is slidably inserted into the insert receiving part 30b. With this configuration, the junction 30 joins the first housing 10 with the second housing 20 so as to bring the second housing 20 to a slidable state with respect to the first housing 10 (that is, so as to set the relative distance between the first housing 10 and the second housing 20 to be changeable) in a state where one side surfaces 10b and 20b (the first opening 10a and the second opening 20a) face each other. Note that the junction 30 may include an inserting part on the second housing 20 and include an insert receiving part on the first housing 10 so as to bring the first housing 10 into a slidable state with respect to the second housing 20, as opposed to the above configuration.

As illustrated in FIGS. 1 and 6, the wireless communication unit 22a can wirelessly communicate with a wireless gateway 71 connected to the network N. The wireless communication unit 22a receives a control signal for controlling the light source 11 from the network N via the wireless gateway 71 and also transmits a measurement result of the spectrometer 21 onto the network N via the wireless gateway 71.

As illustrated in FIG. 1, the data processing server 50 is connected to the network N. The data processing server 50 receives the measurement result of the spectrometer 21 from the network N. The data processing server 50 is a measurement result processing device that performs various data processing related to the received measurement result. The data processing server 50 performs at least one of data analysis, data calculation, and data accumulation on the basis of the received measurement result. For example, the data processing server 50 calculates and accumulates optical properties such as chromaticity and fluorescence properties of the measurement target S. The data processing server 50 transmits the processing result on the network N. The data processing server 50 constitutes a cloud server.

The mobile information terminal 60 is a control terminal having an interface such as a touch panel. An example of the mobile information terminal 60 is a tablet terminal. The mobile information terminal 60 is not particularly limited, and may be a smartphone, a personal computer, or the like. The mobile information terminal 60 generates a control signal to control the light source 11 in accordance with operation (input to the interface) by an operator.

The mobile information terminal 60 is capable of wireless communication with the wireless gateway 72 connected to the network N. The mobile information terminal 60 transmits the generated control signal onto the network via the wireless gateway 72. The mobile information terminal 60 receives various processing results of the data processing server 50 from the network N via the wireless gateway 72. The mobile information terminal 60 displays the received processing result on the interface. This allows the operator to confirm or refer to the processing result.

Next, a method for performing transmitted light measurement of the measurement target S using the spectroscopic measurement device 1 in the spectrometry system 100 will be described.

As illustrated in FIG. 2, first, the junction 30 is used to slide the second housing 20 with respect to the first housing 10 in a direction of allowing the first opening 10a and the second opening 20a to be separated from each other. Next, the measurement target S is disposed between the one side surface 10b of the first housing 10 and the one side surface 20b of the second housing 20, and then, as illustrated in FIG. 3, the second housing 20 is slid with respect to the first housing 10 in a direction to allow the first opening 10a and the second opening 20a to come closer to each other until the measurement target S abuts both the first housing 10 and the second housing 20 (or until a pressing force of a predetermined level or more is generated after the abutment).

Subsequently, as illustrated in FIGS. 1 and 6, an operator operates the mobile information terminal 60 so as to transmit a control signal for driving the light source 11 from the mobile information terminal 60 to the network N. In response to this, the wireless communication unit 22a receives the control signal from the network N, and then, the light source control unit 22b controls the light source 11 to emit the light L1 from the light source 11 on the basis of the control signal The emitted light L1 passes through the first opening 10a to be emitted on the measurement target S. The measurement light L2 as the transmitted light travels toward the second opening 20a and is then received and measured by the spectrometer 21.

The measurement result of the spectrometer 21 is transmitted to the data processing server 50 via the network N by the wireless communication unit 22a. The data processing server 50 performs data processing of the received measurement result. The data processing server 50 transmits the data processing result to the mobile information terminal 60 via the network N. As a result, the processing result received on the mobile information terminal 60 is displayed on the interface.

As described above, the spectroscopic measurement device 1 enables, with its junction 30, the first housing 10 and the second housing 20 to be positioned in a desired positional relationship, and consequently enables the light source 11 housed in the first housing 10 and the spectrometer 21 housed in the second housing 20 to be disposed at desired relative positions with a simple configuration. Additionally, the first housing 10 and the second housing 20 have a light shielding property, and thus, can shield external light without a need to provide a separate configuration. Accordingly, it is possible to arrange the light source 11 and the spectrometer 21 at desired relative positions and downsize the apparatus.

In the spectroscopic measurement device 1, the junction 30 slidably joins the first housing 10 to the second housing 20 in a direction to allow the first opening 10a and the second opening 20a to come closer to or away from each other. With this configuration, the measurement target S can be firmly sandwiched and held by the first opening 10a and the second opening 20a regardless of the thickness of the measurement target S.

The spectrometry system 100 includes the spectroscopic measurement device 1. Therefore, it is possible to obtain the above-described effects of being able to arrange the light source 11 and the spectrometer 21 at desired relative positions and to achieve downsizing of the apparatus. Furthermore, it is possible to have a configuration in which the spectroscopic measurement device 1 has no measurement result processing function, leading to downsizing of the spectroscopic measurement device 1.

The spectrometry system 100 includes: a mobile information terminal 60 configured to generate a control signal for controlling the light source 11 in accordance with operation of an operator and transmit the control signal; a wireless communication unit 22a provided in the spectroscopic measurement device 1 and configured to receive the control signal from the mobile information terminal 60 via the network N; and a light source control unit 22b provided in the spectroscopic measurement device 1 and configured to control the light source 11 on the basis of the control signal received by the wireless communication unit 22a. With this configuration, it is possible to remotely operate the light source 11.

Second Embodiment

Figure 7:
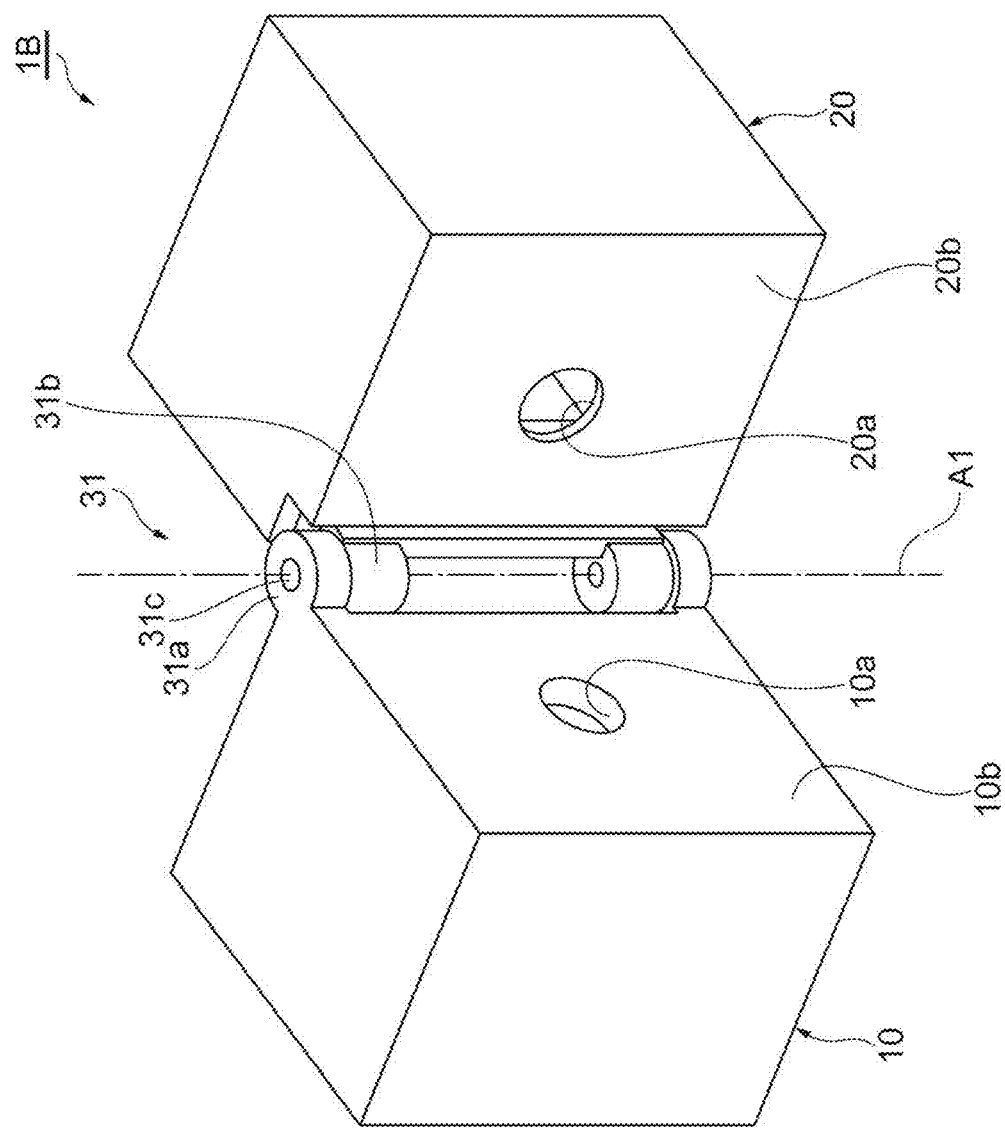
FIG. 7 is a perspective view illustrating a spectroscopic measurement device according to a second embodiment.

Next, a spectroscopic measurement device 1B according to a second embodiment will be described with reference to FIG. 7. In the description of the present embodiment, points different from the first embodiment will be described, and duplicate description will be omitted.

The spectroscopic measurement device 1B includes a junction 31 instead of the junction 30 (refer to FIG. 5). The spectroscopic measurement device 1B can perform reflected light measurement, that is, measurement including emission of the light L1 to the measurement target S and using reflected light reflected by the measurement target S as measurement light L2 corresponding to the light emission. In addition, the spectroscopic measurement device 1B can perform transmitted light measurement when the measurement target S is sufficiently thin. The junction 31 relatively rotatably joins the first housing 10 and the second housing 20 to each other so that the light source 11 of the first housing 10 and the spectrometer 21 of the second housing 20 are disposed at desired relative positions. In performing the reflected light measurement, the desired relative position is a position at which the optical axis of the light L1 emitted on the measurement target S and the optical axis of the measurement light L2 output from the measurement target S intersect at a predetermined angle. In performing the transmitted light measurement, the desired relative position is a position at which the optical axis of the light L1 emitted on the measurement target S and the optical axis of the measurement light L2 output from the measurement target S are coaxial.

The junction 31 can change the relative positions between the first housing 10 and the second housing 20 from the state where the first opening 10a and the second opening 20a face each other and where the optical axis of the light L1 and the optical axis of the measurement light L2 are coaxial to the state where the optical axis of the light L1 and the optical axis of the measurement light L2 intersect each other at a predetermined angle. The junction 31 is configured as a hinge that relatively rotatably joins the first housing 10 and the second housing 20. The junction 31 includes a first pipe portion 31a, a second pipe portion 31b, and a shaft portion 31c.

The first pipe portion 31a has a substantially cylindrical shape. The first pipe portion 31a is provided at both end portions of an edge portion along one side of one side surface 10b of the first housing 10 in such a manner that its axis runs along the one side. The second pipe portion 31b has a substantially cylindrical shape. The second pipe portion 31b is provided at both end portions of an edge portion along one side of one side surface 20b of the second housing 20 in such a manner that its axis runs along the one side. The first pipe portion 31a and the second pipe portion 31b are disposed so that their axes are coaxial (axis A1). The first pipe portion 31a and the second pipe portion 31b are relatively rotatably joined to each other by the shaft portion 31c. The shaft portion 31c may be a shaft, a bolt, or the like.

With the above-described configuration, the junction 31 relatively rotatably joins the first housing 10 and the second housing 20 from the state where the one side surfaces 10b and 20b (the first opening 10a and the second opening 20a) are oriented in the same direction to the state where the one side surface 10b and 20b (the first opening 10a and the second opening 20a) faces each other.

Next, a method of performing reflected light measurement of the measurement target S by using the spectroscopic measurement device 1B will be described.

First, the first housing 10 and the second housing 20 are rotated relative to each other in a direction of allowing the first opening 10a and the second opening 20a to come closer to or away from each other by the junction 31. Next, the spectroscopic measurement device 1B and the measurement target S are disposed so that the measurement target S is located at a point where the optical axis of the light L1 emitted on the measurement target S intersects the optical axis of the measurement light L2 output from the measurement target S.

Subsequently, the light L1 is emitted from the light source 11. The emitted light L1 passes through the first opening 10a to be emitted on the measurement target S. The measurement light L2 as the reflected light travels toward the second opening 20a and is then received and measured by the spectrometer 21.

Next, a method of performing transmitted light measurement of the measurement target S by using the spectroscopic measurement device 1B will be described. Note that the spectroscopic measurement device 1B can perform the transmitted light measurement solely for the measurement target S that is thin enough to set the optical axis of the light L1 to be emitted onto the measurement target S to be substantially coaxial with the optical axis of the measurement light L2 output from the measurement target S even when the measurement target S is disposed between the first housing 10 and the second housing 20.

First, the first housing 10 and the second housing 20 are rotated relative to each other in a direction of allowing the first opening 10a and the second opening 20a to move away from each other by the junction 31. Next, the measurement target S is disposed between the one side surface 10b of the first housing 10 and the one side surface 20b of the second housing 20, and then, the first housing 10 and the second housing 20 are relatively rotated in a direction to allow the first opening 10a and the second opening 20a to come close to each other until the measurement target S abuts both the first housing 10 and the second housing 20 (or until a pressing force of a predetermined level or more is generated after the abutment).

Subsequently, the light L1 is emitted from the light source 11. The emitted light L1 passes through the first opening 10a to be emitted on the measurement target S. The measurement light L2 as the transmitted light travels toward the second opening 20a and is then received and measured by the spectrometer 21.

As described above, it is possible to arrange the light source 11 and the spectrometer 21 at desired relative positions and downsize the apparatus also in the spectroscopic measurement device 1B. Moreover, the spectroscopic measurement device 1B has a configuration in which the junction 31 relatively rotatably joins the first housing 10 and the second housing 20, and thus, it is possible to relatively rotate the first housing 10 accommodating the light source 11 and second housing 20 accommodating the spectrometer 21 so as to arrange the light source 11 and the spectrometer 21 at desired relative angular positions.

In the spectroscopic measurement device 1B, the junction 31 is capable of changing the relative positions to a position at which the first opening 10a and the second opening 20a face each other. Therefore, the transmitted light transmitted through the measurement target S can be received by the spectrometer 21 as the measurement light L2.

In the spectroscopic measurement device 1B, the junction 31 can change the relative position to a position where the optical axis of the light L1 emitted on the measurement target S and the optical axis of the measurement light output from the measurement target S intersect with a predetermined angle. Therefore, the reflected light reflected by the measurement target S can be received by the spectrometer 21 as the measurement light L2.

Third Embodiment

Figure 8:
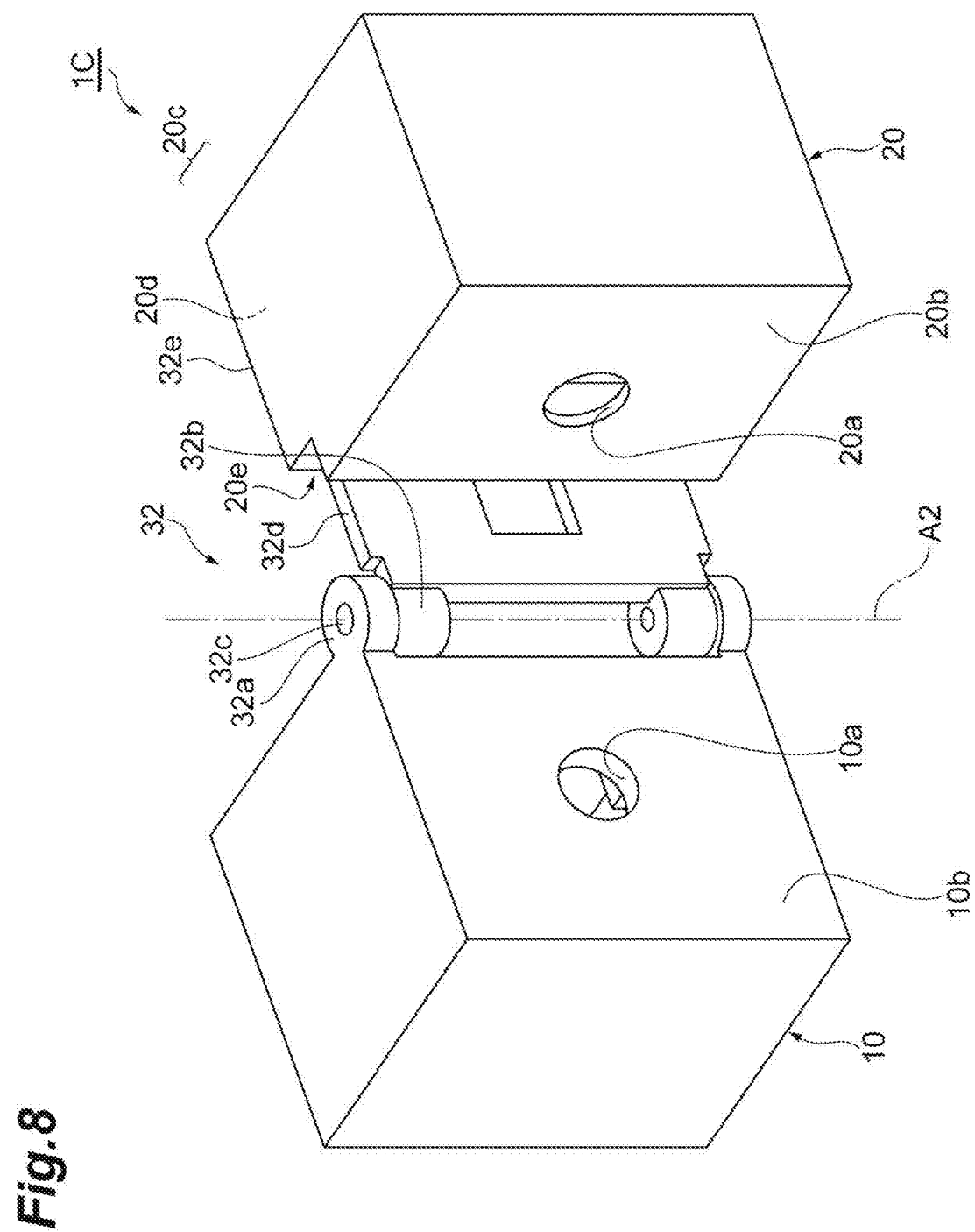
FIG. 8 is a perspective view illustrating a spectroscopic measurement device according to a third embodiment.

Next, a spectroscopic measurement device 1C according to a third embodiment will be described with reference to FIG. 8. In the description of the present embodiment, points different from the first embodiment will be described, and duplicate description will be omitted.

The spectroscopic measurement device 1C includes a junction 32 instead of the junction 30 (refer to FIG. 5). The spectroscopic measurement device 1C can perform reflected light measurement and transmitted light measurement. The junction 32 relatively rotatably joins the first housing 10 and the second housing 20 to each other so that the light source 11 of the first housing 10 and the spectrometer 21 of the second housing 20 are disposed at desired relative positions. Furthermore, the junction 32 slidably joins the second housing 20 with respect to the first housing 10 so that the light source 11 of the first housing 10 and the spectrometer 21 of the second housing 20 are disposed at desired relative positions. In performing the reflected light measurement, the desired relative position is a position at which the optical axis of the light L1 emitted on the measurement target S and the optical axis of the measurement light L2 output from the measurement target S intersect at a predetermined angle. In performing the transmitted light measurement, the desired relative position is a position at which the optical axis of the light L1 emitted on the measurement target S and the optical axis of the measurement light L2 output from the measurement target S are coaxial.

The junction 32 can change the relative positions between the first housing 10 and the second housing 20 from the state where the first opening 10a and the second opening 20a face each other and where the optical axis of the light L1 and the optical axis of the measurement light L2 are coaxial to the state where the optical axis of the light L1 and the optical axis of the measurement light L2 intersect each other at a predetermined angle.

The junction 32 is configured as a hinge that relatively rotatably joins the first housing 10 and the second housing 20. Furthermore, the junction 32 is configured as a sliding mechanism that slidably joins the second housing 20 to the first housing 10. The junction 32 includes a first pipe portion 32a, a second pipe portion 32b, a shaft portion 32c, an inserting part 32d, and an insert receiving part 32e.

The first pipe portion 32a has a substantially cylindrical shape. The first pipe portion 32a is provided at both end portions of an edge portion along one side of one side surface 10b of the first housing 10 so as to run along the one side. The second pipe portion 32b has a substantially cylindrical shape. The second pipe portion 32b is provided at both end portions of an edge portion along one side of one side surface 10b of the first housing 10 in such a manner that its axis runs along the one side, on the proximal end side of the inserting part 32d. The first pipe portion 32a and the second pipe portion 32b are disposed so that their axes are coaxial with each other (axis A2). The first pipe portion 32a and the second pipe portion 32b are relatively rotatably joined to each other by the shaft portion 32c. The shaft portion 32c may be a shaft, a bolt, or the like.

The inserting part 32d is provided on an edge portion along one side of the one side surface 10b of the first housing 10 via the first pipe portion 32a and the second pipe portion 32b joined by the shaft portion 32c. The inserting part 32d is provided so as to protrude in a rectangular flat plate shape. The inserting part 32d has a rectangular cutout formed to open to the distal end side and having a rectangular shape when viewed in a thickness direction of the inserting part 32d. The cutout of the inserting part 32d is provided in a central portion of the inserting part 32d in the direction along the one side of the one side surface 10b.

The insert receiving part 32e is a recess (hole) formed along one side on an adjacent other side surface 20d on the one side surface 20b of the second housing 20. The insert receiving part 32e is formed in a rectangular cross section corresponding to the shape of the inserting part 32d, on the side wall portion 20c on the other side surface 20d side of the second housing 20. The insert receiving part 32e is provided on a bottom surface of a stepped portion 20e formed by cutting out an edge portion along the one side of the one side surface 20b.

The insert receiving part 32e communicates with a cutout formed in the side wall portion 20c. The cutout of the insert receiving part 32e opens on the bottom surface of the stepped portion 20e and is formed in a rectangular shape when it is viewed from the other side surface 20d. The cutout of the insert receiving part 32e is provided in the central portion of the other side surface 20d in the direction along the one side of the one side surface 20b. As will be described below, the cutout o the insert receiving part 32e is formed at a position corresponding to the position of the cutout of the inserting part 32d in a state where the inserting part 32d is inserted in the insert receiving part 32e. The cable C can be pulled out from the inside of the second housing 20 to the outside via the these cutouts.

In the above configuration, the junction 32 is in a state where the inserting part 32d is slidably inserted into the insert receiving part 32e. With this configuration, the junction 32 joins the first housing 10 with the second housing 20 so as to bring the second housing 20 to a slidable state with respect to the first housing 10 (that is, so as to set the relative distance between the first housing 10 and the second housing 20 to be changeable). Note that the junction 32 may include an inserting part on the second housing 20 and include an insert receiving part on the first housing 10 so as to bring the first housing 10 into a slidable state with respect to the second housing 20, as opposed to the above configuration.

Furthermore, the junction 32 relatively rotatably joins the first housing 10 and the second housing 20 from the state where the one side surfaces 10b and 20b (the first opening 10a and the second opening 20a) are oriented in the same direction to the state where the one side surface 10b and 20b (the first opening 10a and the second opening 20a) faces each other.

Next, a method of performing reflected light measurement of the measurement target S by using the spectroscopic measurement device 1C will be described.

First, the junction 32 is used to slide the second housing 20 with respect to the first housing 10 so as to adjust the first housing 10 and the second housing 20 to be disposed with an appropriate interval. Next, the first housing 10 and the second housing 20 are rotated relative to each other in a direction of allowing the first opening 10a and the second opening 20a to come closer to or away from each other by the junction 32. Next, the spectroscopic measurement device 1C and the measurement target S are disposed so that the measurement target S is located at a point where the optical axis of the light L1 emitted on the measurement target S intersects the optical axis of the measurement light L2 output from the measurement target S.

Subsequently, the light L1 is emitted from the light source 11. The emitted light L1 passes through the first opening 10a to be emitted on the measurement target S. The measurement light L2 as the reflected light travels toward the second opening 20a and is then received and measured by the spectrometer 21.

Next, a method of performing transmitted light measurement of the measurement target S by using the spectroscopic measurement device 1C will be described.

First, the junction 32 is used to relatively rotate the first housing 10 and the second housing 20 in a direction of allowing the first opening 10a and the second opening 20a to come closer to or away from each other so as to set the optical axis of the light L1 emitted onto the measurement target S and the optical axis of the measurement light L2 output from the measurement target S to be coaxial. Next, the measurement target S is disposed between the one side surface 10b of the first housing 10 and the one side surface 20b of the second housing 20, and then, the first housing 10 and the second housing 20 are relatively rotated in a direction to allow the first opening 10a and the second opening 20a to come close to each other until the measurement target S abuts both the first housing 10 and the second housing 20 (or until a pressing force of a predetermined level or more is generated after the abutment).

Subsequently, the light L1 is emitted from the light source 11. The emitted light L1 passes through the first opening 10a to be emitted on the measurement target S. The measurement light L2 as the transmitted light travels toward the second opening 20a and is then received and measured by the spectrometer 21.

As described above, it is possible to arrange the light source 11 and the spectrometer 21 at desired relative positions and downsize the apparatus also in the spectroscopic measurement device 1C. Moreover, the spectroscopic measurement device 1C has a configuration in which the junction 32 relatively rotatably joins the first housing 10 and the second housing 20, and thus, it is possible to relatively rotates the first housing 10 accommodating the light source 11 and second housing 20 accommodating the spectrometer 21 so as to arrange the light source 11 and the spectrometer 21 at desired relative angular positions.

In the spectroscopic measurement device 1C, the junction 32 slidably joins the first housing 10 to the second housing 20 in a direction to allow the first opening 10a and the second opening 20a to come closer to or away from each other. With this configuration, the measurement target S can be firmly sandwiched and held by the first opening 10a and the second opening 20a regardless of the thickness of the measurement target S.

In the spectroscopic measurement device 1C, the junction 32 is capable of changing the relative positions to a position at which the first opening 10a and the second opening 20a face each other. Therefore, the transmitted light transmitted through the measurement target S can be received by the spectrometer 21 as the measurement light L2.

In the spectroscopic measurement device 1C, the junction 32 can change the relative position to a position where the optical axis of the light L1 emitted on the measurement target S and the optical axis of the measurement light output from the measurement target S intersect with a predetermined angle. Therefore, the reflected light reflected by the measurement target S can be received by the spectrometer 21 as the measurement light L2.

While one embodiment of the present invention has been described hereinabove, the present invention is not limited to the above-described embodiments, but may include modifications and other applications obtained within the spirit and scope described in individual claims.

First Modification

Figure 9:
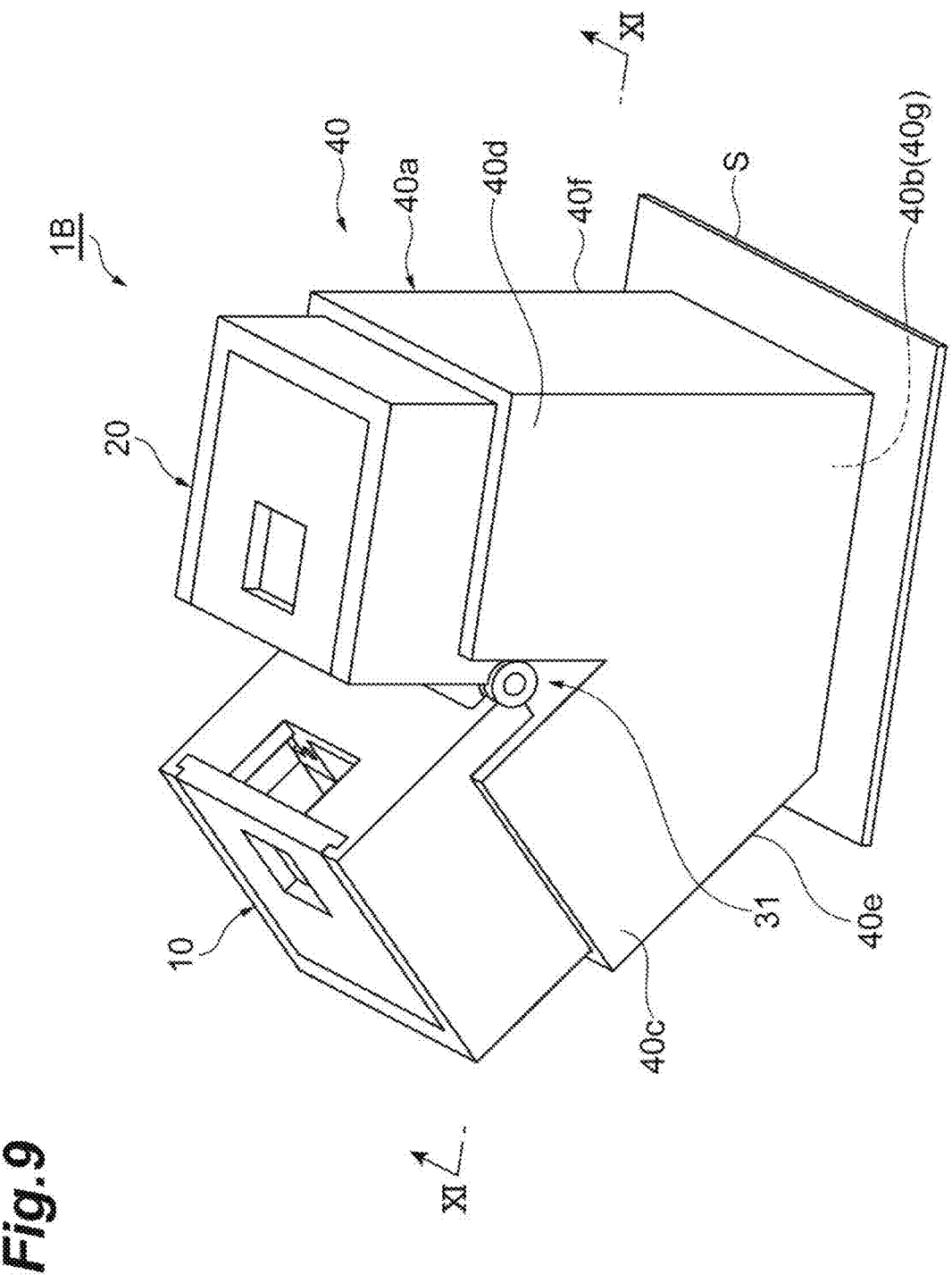
FIG. 9 is a configuration diagram illustrating a spectroscopic measurement device according to a modification.
Figure 10:
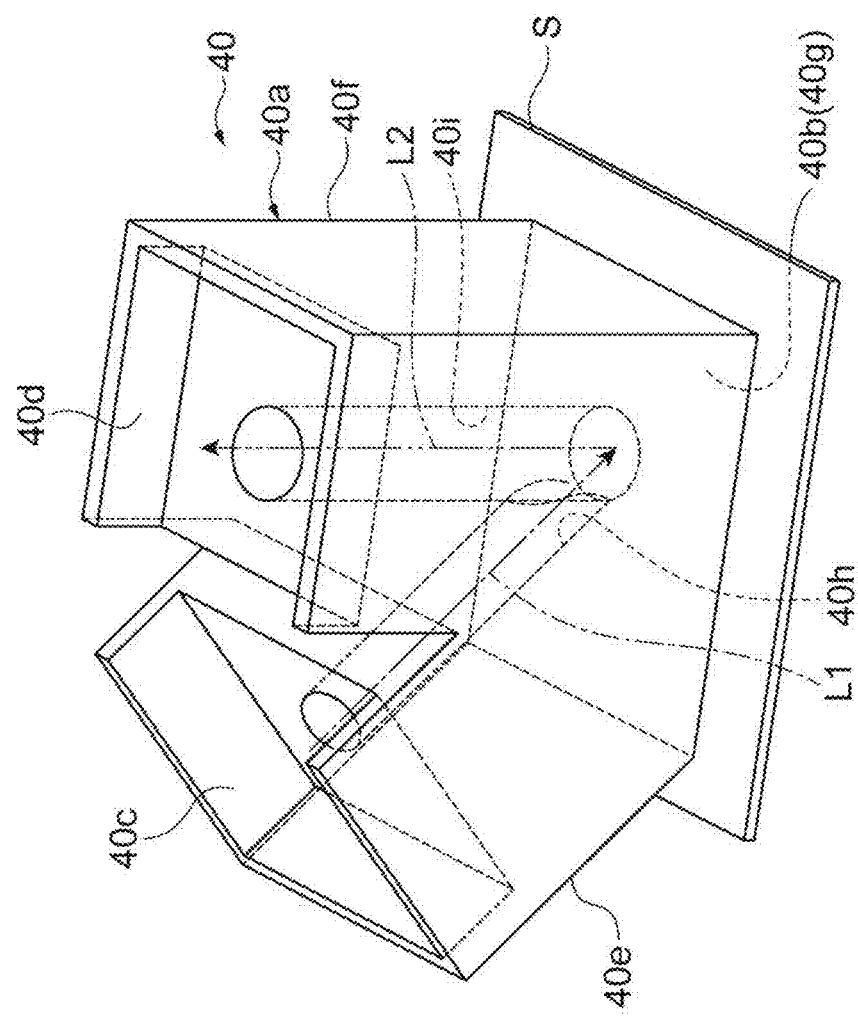
FIG. 10 is a perspective view illustrating a first optical path and a second optical path provided in an attachment of the spectroscopic measurement device of FIG. 9.
Figure 11:
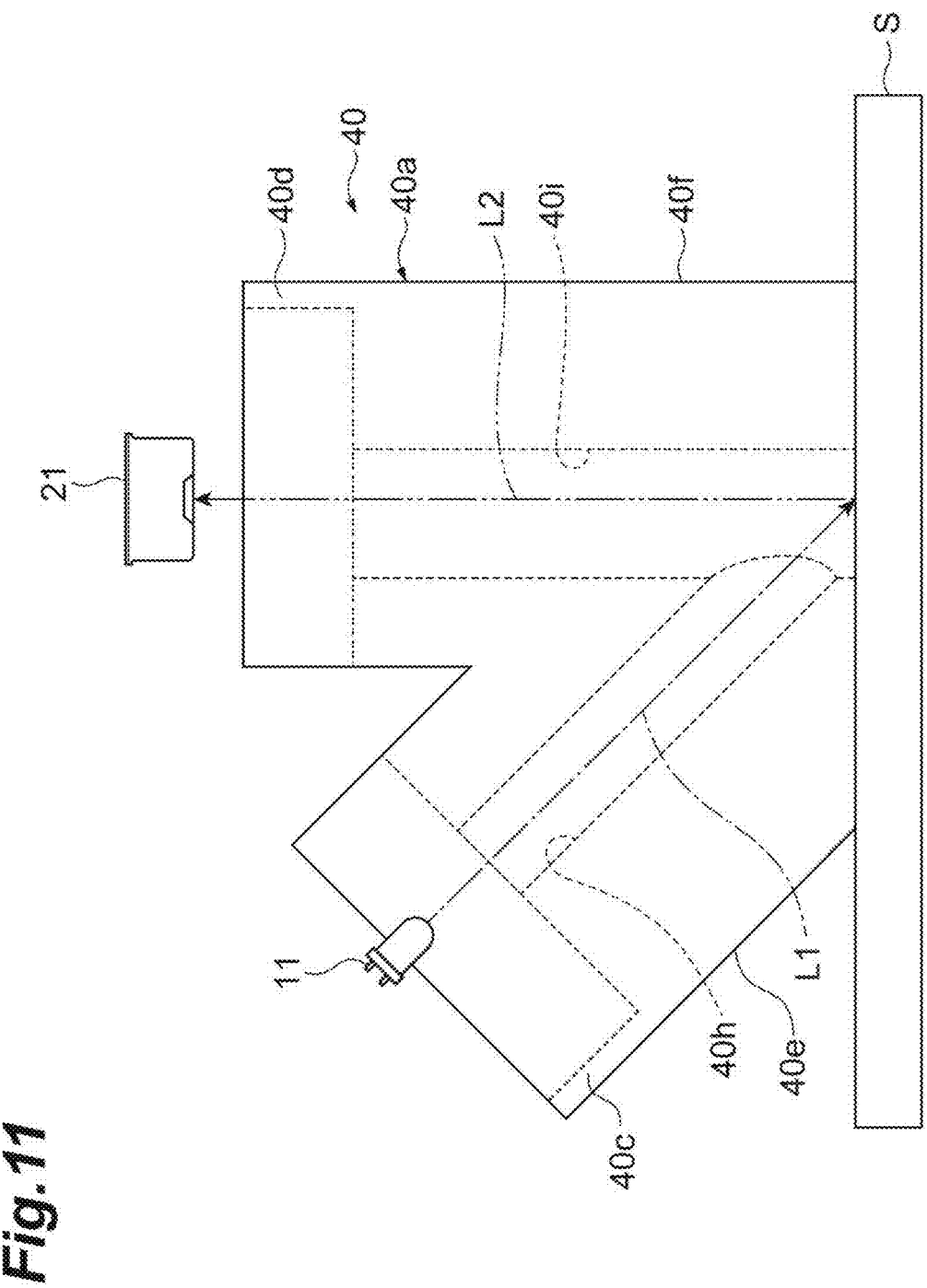
FIG. 11 is a view schematically illustrating a cross section taken along line XI-XI of FIG. 9.

As illustrated in FIGS. 9, 10, and 11, the spectroscopic measurement device 1B according to the second embodiment may further include an attachment 40. The attachment 40 makes it easy to hold the light source 11 of the first housing 10 and the spectrometer 21 of the second housing 20 in a state of being disposed in desired relative positions for performing reflected light measurement. The desired relative position is a position at which the optical axis of the light L1 emitted on the measurement target S and the optical axis of the measurement light L2 output from the measurement target S intersect at a predetermined angle (here, 45 degrees). In the following description, for the sake of convenience, the side away from the measurement target S will be referred to as "upper side" and the side closer to the measurement target S will be described as "lower side".

The attachment 40 detachably holds the first housing 10 and the second housing 20 so that the light source 11 of the first housing 10 and the spectrometer 21 of the second housing 20 are disposed at desired relative positions. The attachment 40 includes a main body 40a, a first holding part 40c, and a second holding part 40d. The main body 40a is a block member including a planar lower surface 40b. The main body 40a has a configuration in which the main body 40a is mounted on the measurement target S, and this configuration allows the lower surface 40b in contact with the measurement target S to function as a position regulator 40g that regulates the position of the measurement target S. The main body 40a includes: a first columnar member 40e having a quadrangular prism-like outer shape having an axial direction inclined with respect to the lower surface 40b; a second columnar member 40f having a quadrangular columnar shape having an axial direction orthogonal to the lower surface 40b. The first holding part 40c is provided on the upper surface of the first columnar member 40e, while the second holding part 40d is provided on the upper surface of the second columnar member 40f.

The first holding part 40c detachably holds the first housing 10 with respect to the main body 40a. The first holding part 40c includes a wall portion upright on the upper surface of the first columnar member 40e. The wall portion constituting the first holding part 40c is formed so as to be engaged with the first housing 10 on three sides except for the second holding part 40d side. The attachment 40 uses the first holding part 40c to hold the first housing 10 in a state where the first opening 10a faces the main body 40a side (upper surface side of the first columnar member 40e). The first housing 10 may be detachably secured to the main body 40a or the first holding part 40c by a screw or the like.

The second holding part 40d detachably holds the second housing 20 with respect to the main body 40a. The second holding part 40d includes a wall portion upright on the upper surface of the second columnar member 40f. The wall portion constituting the second holding part 40d is formed so as to be engaged with the second housing 20 on three sides except for the side of the first holding part 40c. The attachment 40 uses the second holding part 40d to hold the second housing 20 in a state where the second opening 20a faces the main body 40a side (upper surface side of the second columnar member 40f). The second housing 20 may be detachably secured to the main body 40a or the second holding part 40d by a screw or the like.

The distance between the first holding part 40c and the second holding part 40d is set to a distance that enables simultaneously holding the first housing 10 and the second housing 20 of the spectroscopic measurement device 1B (that is, the first housing 10 and the second housing 20 joined by the junction 31).

As illustrated in FIGS. 10 and 11, the main body 40a internally includes: a first optical path 40h being an optical path of the light L1 emitted onto the measurement target S and continuous with the first opening 10a; and a second optical path 40i being an optical path of the measurement light L2 output from the measurement target S and continuous with the second opening 20a.

One end of the first optical path 40h opens to the upper surface of the first columnar member 40e. The other end of the first optical path 40h opens to the lower surface 40b of the main body 40a. One end of the second optical path 40i opens to the upper surface of the second columnar member 40f. The other end of the second optical path 40i opens to the same region as the other end of the first optical path 40h, out of the lower surface 40b of the main body 40a. That is, the other end of the first optical path 40h and the other end of the second optical path 40i share an opening portion on the lower surface 40b of the main body 40a. The angle between the first optical path 40h and the second optical path 40i is set to a predetermined angle in accordance with the measurement application. Here, the angle between the first optical path 40h and the second optical path 40i is set to 45 degrees as an example, but it is not limited thereto, and may be set to 90 degrees, for example.

The attachment 40 has a light shielding property. Here, the attachment 40 is formed of resin having high light shielding property so as not to obstruct wireless communication by a wireless communication unit 22a.

Next, a method of performing reflected light measurement of the measurement target S by using the spectroscopic measurement device 1B according to the present modification will be described.

First, as illustrated in FIG. 9, the attachment 40 is mounted on the measurement target S. Next, the first housing 10 is mounted on the first holding part 40c so that the first opening 10a faces the upper surface of the first columnar member 40e. The second housing 20 is mounted on the second holding part 40d so that the second opening 20a faces the upper surface of the second columnar member 40f. With this configuration, the optical axis of the light L1 emitted on the measurement target S and the optical axis of the measurement light L2 output from the measurement target S are set to intersect each other at a predetermined angle (here, 45 degrees) at a point corresponding to the other end of the first optical path 40h opened in the lower surface 40b of the main body 40a (that is, the other end of the second optical path 40i).

Subsequently, the light L1 is emitted from the light source 11. The emitted light L1 passes through the first opening 10a and the first optical path 40h to be emitted on the measurement target S. The measurement light L2 as the reflected light passes the second optical path 40i and travels toward the second opening 20a, so as to be received and measured by the spectrometer 21.

As described above, it is possible to arrange the light source 11 and the spectrometer 21 at desired relative positions and downsize the apparatus also in the spectroscopic measurement device 1B according to the present modification. Moreover, since the spectroscopic measurement device 1B further includes the attachment 40 configured to detachably hold the first housing 10 and the second housing 20 joined by the junction 31, making it possible to use the attachment 40 to hold the first housing 10 and the second housing 20 positioned in a desired positional relationship by the junction 31.

In the spectroscopic measurement device 1B according to the present modification, the attachment 40 has a light shielding property, and the attachment 40 internally includes the first optical path 40h and the second optical path 40i. The configuration, in this case, would suppress invasion of external light into the first optical path 40h and the second optical path 40i provided inside the attachment 40.

In the spectroscopic measurement device 1B according to the present modification, the attachment 40 has a lower surface 40b that functions as the position regulator 40g that regulates the position of the measurement target S. Therefore, it is possible to use the position regulator 40g to hold the measurement target S.

It has been described that the spectroscopic measurement device 1B according to the second embodiment may further include the attachment 40. Alternatively, however, the spectroscopic measurement device 1C according to the third embodiment may further include the attachment 40.

Second Modification

Figure 12:
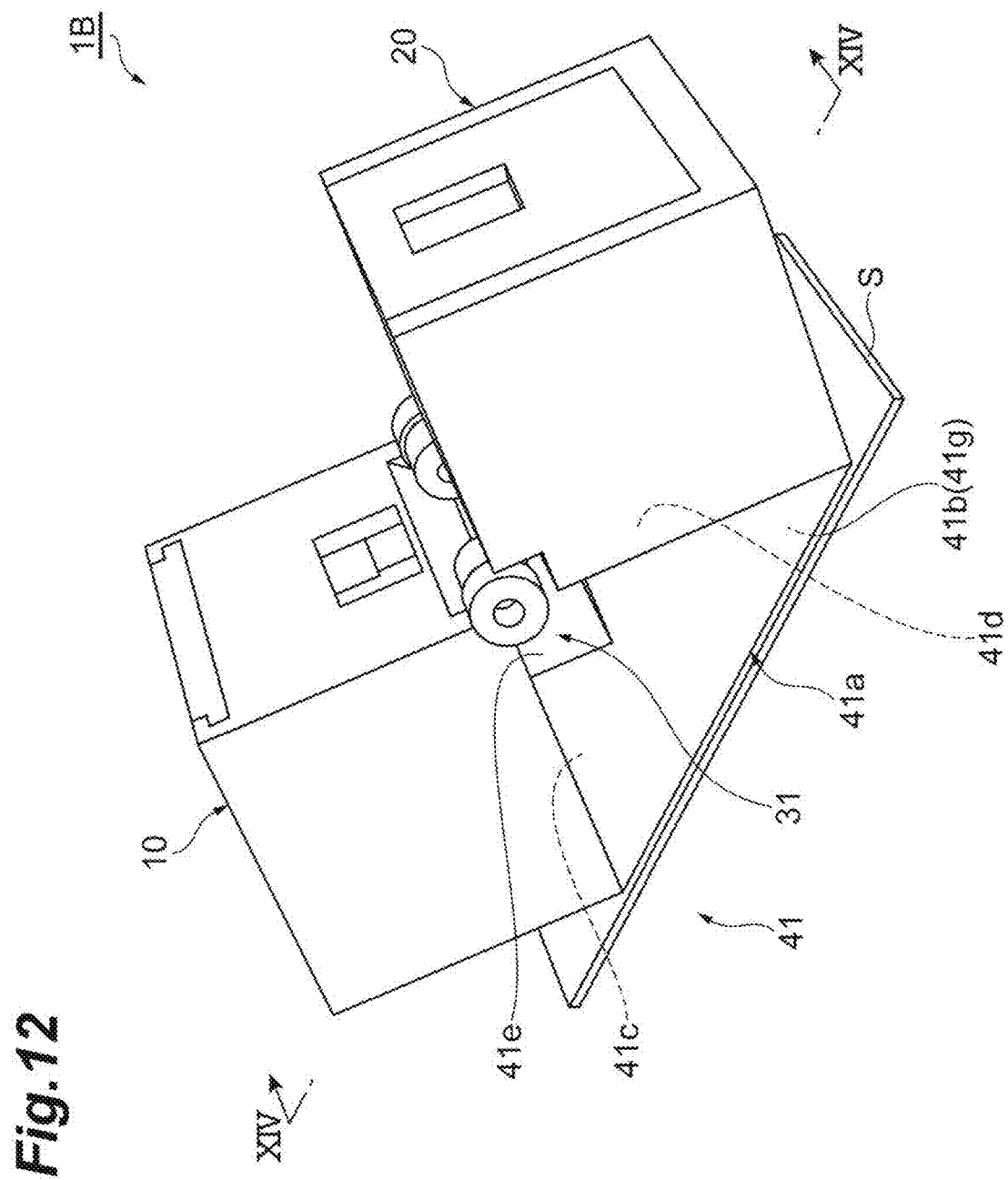
FIG. 12 is a configuration diagram illustrating a spectroscopic measurement device according to a modification.
Figure 13:
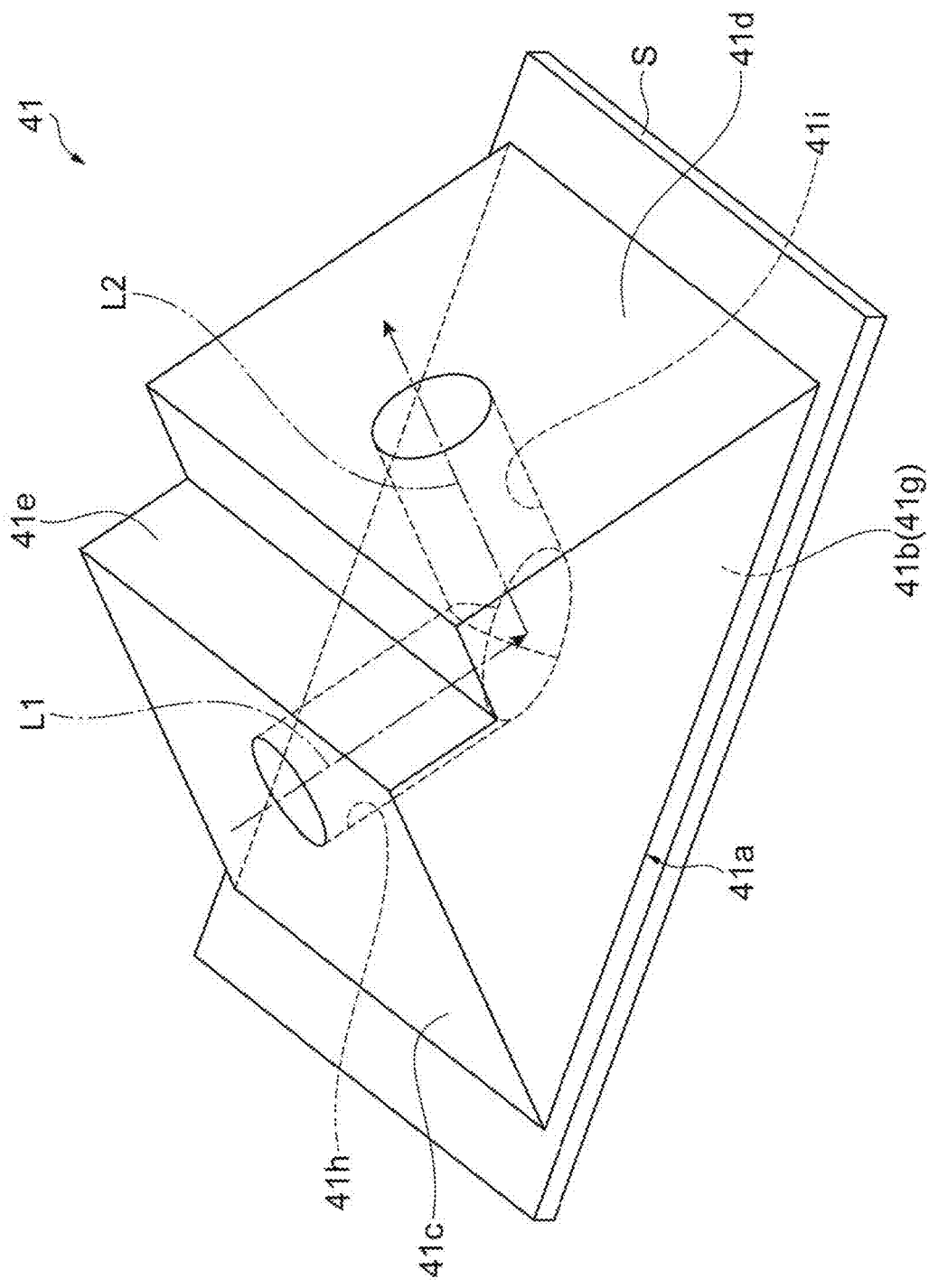
FIG. 13 is a perspective view illustrating a first optical path and a second optical path provided in an attachment of the spectroscopic measurement device of FIG. 12.
Figure 14:
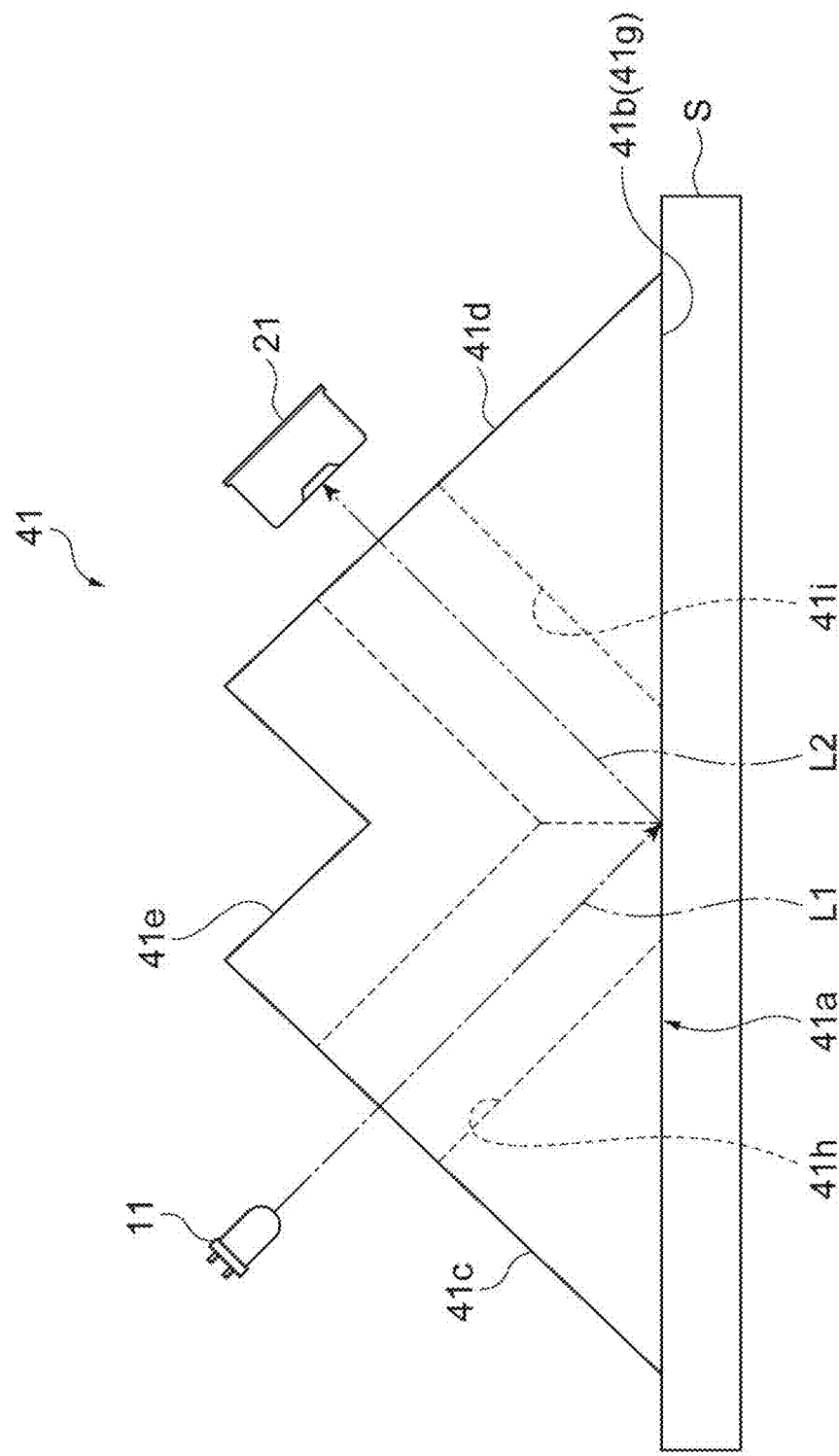
FIG. 14 is a diagram schematically illustrating a cross section taken along line XIV-XIV of FIG. 12.

As illustrated in FIGS. 12, 13, and 14, the spectroscopic measurement device 1B of the second embodiment may further include an attachment 41. The attachment 41 makes it easy to hold the light source 11 of the first housing 10 and the spectrometer 21 of the second housing 20 in a state of being disposed in desired relative positions for performing reflected light measurement. The desired relative position is a position at which the optical axis of the light L1 emitted on the measurement target S and the optical axis of the measurement light L2 output from the measurement target S intersect at a predetermined angle (here, 90 degrees). In the following description, for the sake of convenience, the side away from the measurement target S will be referred to as "upper side" and the side closer to the measurement target S will be described as "lower side".

The attachment 41 detachably holds the first housing 10 and the second housing 20 so that the light source 11 of the first housing 10 and the spectrometer 21 of the second housing 20 are disposed at desired relative positions. The attachment 41 includes a main body 41a, an slope 41c, and an slope 41d. The main body 41a is a block member including a planar lower surface 41b. The main body 41a has a configuration in which the main body 41a is mounted on the measurement target S, and this configuration allows the lower surface 41b in contact with the measurement target S to function as a position regulator 41g that regulates the position of the measurement target S. The main body 41a has a substantially triangular prism shape. Specifically, the main body 41a has an isosceles triangular prism shape having side surfaces, namely, the lower surface 41b and a pair of slopes 41c and 41d each of which being inclined by 45 degrees with respect to the lower surface 41b and intersecting with each other.

The main body 41a has, in its upper portion, a cutout 41e extending in axial directions. The cutout 41a is a space including a plane orthogonal to the slope 41c and a plane perpendicular to the slope 41d. The cutout 41e is formed at a position corresponding to a right angle corner of the isosceles triangular prism shape.

The slope 41c functions as a first holding part to detachably hold the first housing 10 with respect to the main body 41a. The attachment 41 holds the first housing 10 in a state where the slope 41c allows the first opening 10a to face the main body 41a side (the slope 41c side). In contrast, the slope 41d functions as a second holding part to detachably hold the second housing 20 with respect to the main body 41a. The attachment 41 holds the second housing 20 in a state where the slope 41d allows the second opening 20a to face the main body 41a side (the slope 41d side).

Specifically, first, an extending direction of the cutout 41e of the main body 41a is defined as the axis A1 (refer to FIG. 7) of the junction 31, and the junction 31 is disposed in the cutout 41e in this state. With this configuration, it is possible to avoid interference that would occur between the first pipe portion 31a/the second pipe portion 31b constituting the junction 31, and the main body 41a. In this state, the first housing 10 is mounted on the slope 41c, and the second housing 20 is mounted on the slope 41d. With this arrangement, the first housing 10 is supported by the slope 41c while the second housing 20 is supported by the slope 41d. At this time, the junction 31 is pulled in individual directions by a component along the slope 41c of the gravity acting on the first housing 10 and a component along the slope 41d of the gravity acting on the second housing 20. As a result, forces acting on the first housing 10 and the second housing 20 joined by the junction 31 are balanced, so as to be able to stably and detachably hold the two housings on the attachment 41.

It would be also possible to provide a cylindrical protrusion on the slope 41c and a recess to be engaged with the protrusion on one side surface 10b of the first housing 10, so as to position the first housing 10 on the slope 41c. It would be also possible to provide a cylindrical protrusion on the slope 41d and a recess to be engaged with the protrusion on one side surface 20b of the second housing 20, so as to position the second housing 20 on the second holding part 42c. The first housing 10 and the second housing 20 may be detachably secured to the main body 41a by a screw or the like.

As illustrated in FIGS. 13 and 14, the main body 41a internally includes: a first optical path 41h being an optical path of the light L1 emitted onto the measurement target S and continuous with the first opening 10a; and a second optical path 41i being an optical path of the measurement light L2 output from the measurement target S and continuous with the second opening 20a.

One end of the first optical path 41h opens to the slope 41c. The other end of the first optical path 41h opens to the lower surface 41b of the main body 41a. One end of the second optical path 41i opens to the slope 41d. The other end of the second optical path 41i opens to the same region as the other end of the first optical path 41h, out of the lower surface 41b of the main body 41a. That is, the other end of the first optical path 41h and the other end of the second optical path 41i share an opening portion on the lower surface 41b of the main body 41a. The angle between the first optical path 41h and the second optical path 41i is set to a predetermined angle in accordance with the measurement application. Here, the angle between the first optical path 41h and the second optical path 41i is set to 90 degrees as an example, but it is not limited thereto, and may be set to 45 degrees, for example.

The attachment 41 has a light shielding property. The attachment 41 here is formed of a resin having high light shielding property so as not to hamper wireless communication by the wireless communication unit 22a.

Next, a method of performing reflected light measurement of the measurement target S by using the spectroscopic measurement device 1B according to the present modification will be described.

First, as illustrated in FIG. 12, the attachment 41 is mounted on the measurement target S. Next, the first housing 10 and the second housing 20 joined by the junction 31 are arranged such that the junction 31 is mounted at the cutout 41e portion of the main body 41a, the first housing 10 is mounted on the slope 41c, and the second housing 20 is mounted on the slope 41d. At this time, the first opening 10a is set to face the main body 41a side and the second opening 20a is set to face the main body 41a side. With this configuration, the optical axis of the light L1 emitted on the measurement target S and the optical axis of the measurement light L2 output from the measurement target S are set to intersect each other at a predetermined angle (here, 90 degrees) at a point corresponding to the other end of the first optical path 41h opened in the lower surface 41b of the main body 41a (that is, the other end of the second optical path 41i).

Subsequently, the light L1 is emitted from the light source 11. The emitted light L1 passes through the first opening 10a and the first optical path 41h to be emitted on the measurement target S. The measurement light L2 as the reflected light passes the second optical path 41i and travels toward the second opening 20a, so as to be received and measured by the spectrometer 21.

As described above, it is possible to arrange the light source 11 and the spectrometer 21 at desired relative positions and downsize the apparatus also in the spectroscopic measurement device 1B according to the present modification. Moreover, since the spectroscopic measurement device 1B further includes the attachment 41 to detachably hold the first housing 10 and the second housing 20 joined by the junction 31, making it possible to use the attachment 41 to hold the first housing 10 and the second housing 20 positioned in a desired positional relationship by the junction 31.

In the spectroscopic measurement device 1B according to the present modification, the attachment 41 has a light shielding property, and the attachment 41 internally includes the first optical path 41h and the second optical path 41i. The configuration, in this case, would suppress invasion of external light into the first optical path 41h and the second optical path 41i provided inside the attachment 41.

In the spectroscopic measurement device 1B according to the present modification, the attachment 41 has a lower surface 41b that functions as the position regulator 41g that regulates the position of the measurement target S. Therefore, it is possible to use the position regulator 41g to hold the measurement target S.

It has been described that the spectroscopic measurement device 1B according to the second embodiment may further include the attachment 41. Alternatively, however, the spectroscopic measurement device 1C according to the third embodiment may further include the attachment 41.

Third Modification

Figure 15:
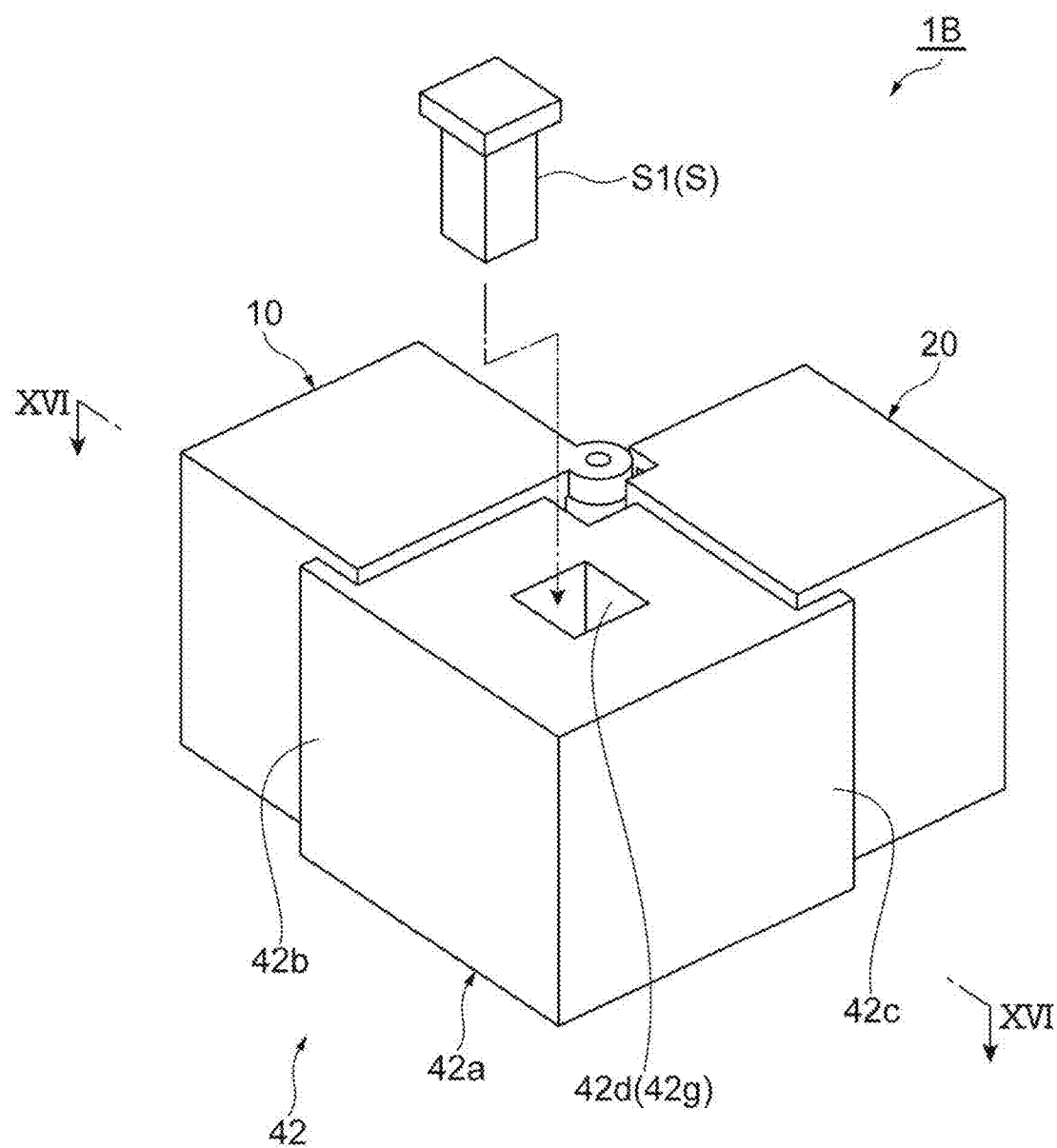
FIG. 15 is a configuration diagram illustrating a spectroscopic measurement device according to a modification.
Figure 16:
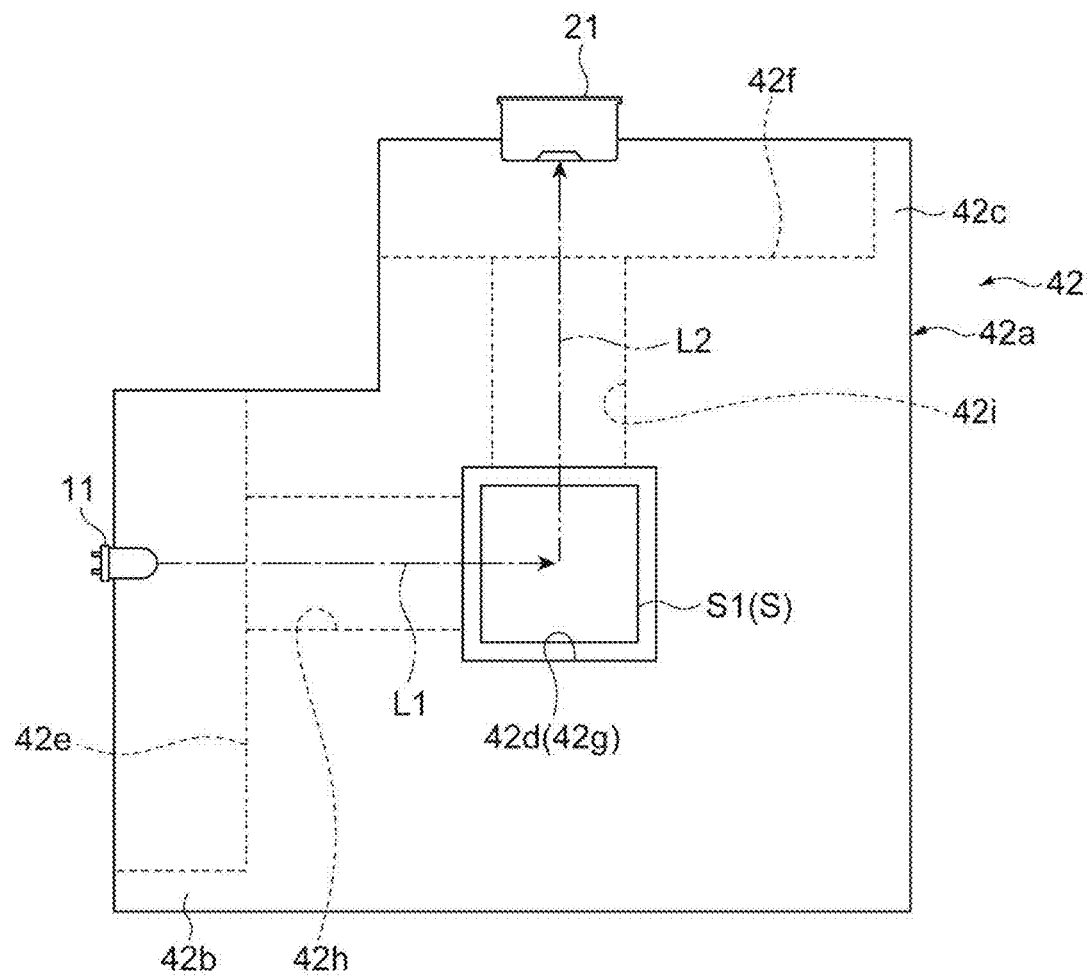
FIG. 16 is a diagram schematically illustrating a cross section taken along line XVI-XVI of FIG. 15.

As illustrated in FIGS. 15 and 16, the spectroscopic measurement device 1B of the second embodiment may further include an attachment 42. The attachment 42 makes it easy to hold the light source 11 of the first housing 10 and the spectrometer 21 of the second housing 20 in a state of being disposed in desired relative positions for performing fluorescence measurement. The desired relative position is a position at which the optical axis of the light L1 emitted onto a cuvette S1 containing the measurement target S and the optical axis of the measurement light L2 output from the measurement target S intersect at a predetermined angle (here, 90 degrees). The cuvette S1 herein is a container formed of a transparent member (glass, resin, quartz, or the like) that transmits the light L1 and the measurement light L2, and accommodates the measurement target S. In the following description, the upper side (cap side) of the cuvette S1 will be referred to as "upper side" and the opposite side will be described as "lower side" for the sake of convenience.

The attachment 42 detachably holds the first housing 10 and the second housing 20 so that the light source 11 of the first housing 10 and the spectrometer 21 of the second housing 20 are disposed at desired relative positions. The attachment 42 includes a main body 42a, a first holding part 42b, and a second holding part 42c. The main body 42a is a block member having a substantially parallelepiped shape. The upper surface of the main body 42a has a recess 42d formed to have a rectangular cross section. The cuvette S1 having a predetermined external dimension is fitted into the recess 42d. In other words, the cuvette S1 can be inserted into the recess 42d without a gap.

The first holding part 42b detachably holds the first housing 10 with respect to the main body 42a. The first holding part 42b includes a wall portion upright on a portion (L-shaped edge portion) of the edge portion on one side surface 42e of the main body 42a. The first housing 10 is positioned on the one side surface 42e by the first holding part 42b and is detachably secured to the main body 42a or the first holding part 42b by a screw or the like. Note that the first holding part 42b may hold the first housing 10 by engaging with the first housing 10.

The second holding part 42c detachably holds the second housing 20 with respect to the main body 42a. The second holding part 42c includes a wall portion upright on a part of the edge portion (L-shaped edge portion) on another side surface 42f adjacent to the one side surface 42e of the main body 42a. The second housing 20 is positioned on the other side surface 42f by the second holding part 42c and is detachably secured to the main body 42a or the second holding part 42c by a screw or the like. Note that the second holding part 42c may hold the second housing 20 by engaging with the second housing 20.

As illustrated in FIG. 16, the main body 42a internally includes: a first optical path 42h being an optical path of the light L1 emitted onto the cuvette S1 and continuous with the first opening 10a; and a second optical path 42i being an optical path of the measurement light L2 output from the measurement target S and continuous with the second opening 20a. One end of the first optical path 42h opens to the one side surface 42e of the main body 42a. The other end of the first optical path 42h opens to the inner wall surface of the recess 42d of the main body 42a. One end of the second optical path 42i opens to the other side surface 42f of the main body 42a. The other end of the second optical path 42i opens to the other surface adjacent to the inner wall surface of the recess 42d of the main body 42a. The angle between the first optical path 42h and the second optical path 42i is set to a predetermined angle in accordance with the measurement application. Here, the angle between the first optical path 42h and the second optical path 42i is set to 90 degrees as an example, but it is not limited thereto, and may be set to 45 degrees, for example.

The attachment 42 has a light shielding property. The attachment 42 here is formed of a resin having high light shielding property so as not to hamper wireless communication by the wireless communication unit 22a.

Next, a method of performing fluorescence measurement of the measurement target S contained in the cuvette S1 by using the spectroscopic measurement device 1B according to the present modification will be described.

First, as illustrated in FIG. 15, the first housing 10 is held by the first holding part 42b so that the first opening 10a faces the side surface 42e side (the first holding part 42b side) of the main body 42a. The second housing 20 is held by the second holding part 42c so that the second opening 20a faces the other side surface 42f side (the second holding part 42c side) of the main body 42a. Next, the cuvette S1 is fitted into the recess 42d. With this configuration, the optical axis of the light L1 emitted on the measurement target S contained in the cuvette S1 and the optical axis of the measurement light L2 (fluorescence) output from the measurement target S intersect with each other at a predetermined angle (here, 90 degrees) at a center of the recess 42d of the main body 42a in plan view.

Subsequently, the light L1 is emitted from the light source 11. The emitted light L1 passes through the first opening 10a and the first optical path 42h to be emitted on the measurement target S. The measurement light L2 as the fluorescence passes the second optical path 42i and travels toward the second opening 20a, so as to be received and measured by the spectrometer 21.

As described above, it is possible to arrange the light source 11 and the spectrometer 21 at desired relative positions and downsize the apparatus also in the spectroscopic measurement device 1B according to the present modification. Moreover, since the spectroscopic measurement device 1B further includes the attachment 42 to detachably hold the first housing 10 and the second housing 20 joined by the junction 31, making it possible to use the attachment 42 to hold the first housing 10 and the second housing 20 positioned in a desired positional relationship by the junction 31.

The spectroscopic measurement device 1B according to the present modification can allow the recess 42d of the attachment 42 to function as a position regulator 42g for regulating the position of the inserted cuvette S1, enabling the cuvette S1 to be reliably held in the recess 42d.

In the spectroscopic measurement device 1B according to the present modification, the attachment 42 has a light shielding property, and the attachment 42 internally includes the first optical path 42*h* and the second optical path 42*i*. The configuration, in this case, makes it possible to suppress invasion of external light into the first optical path 42*h* and the second optical path 42*i* provided inside the attachment 42.

Fourth Modification

Figure 17:
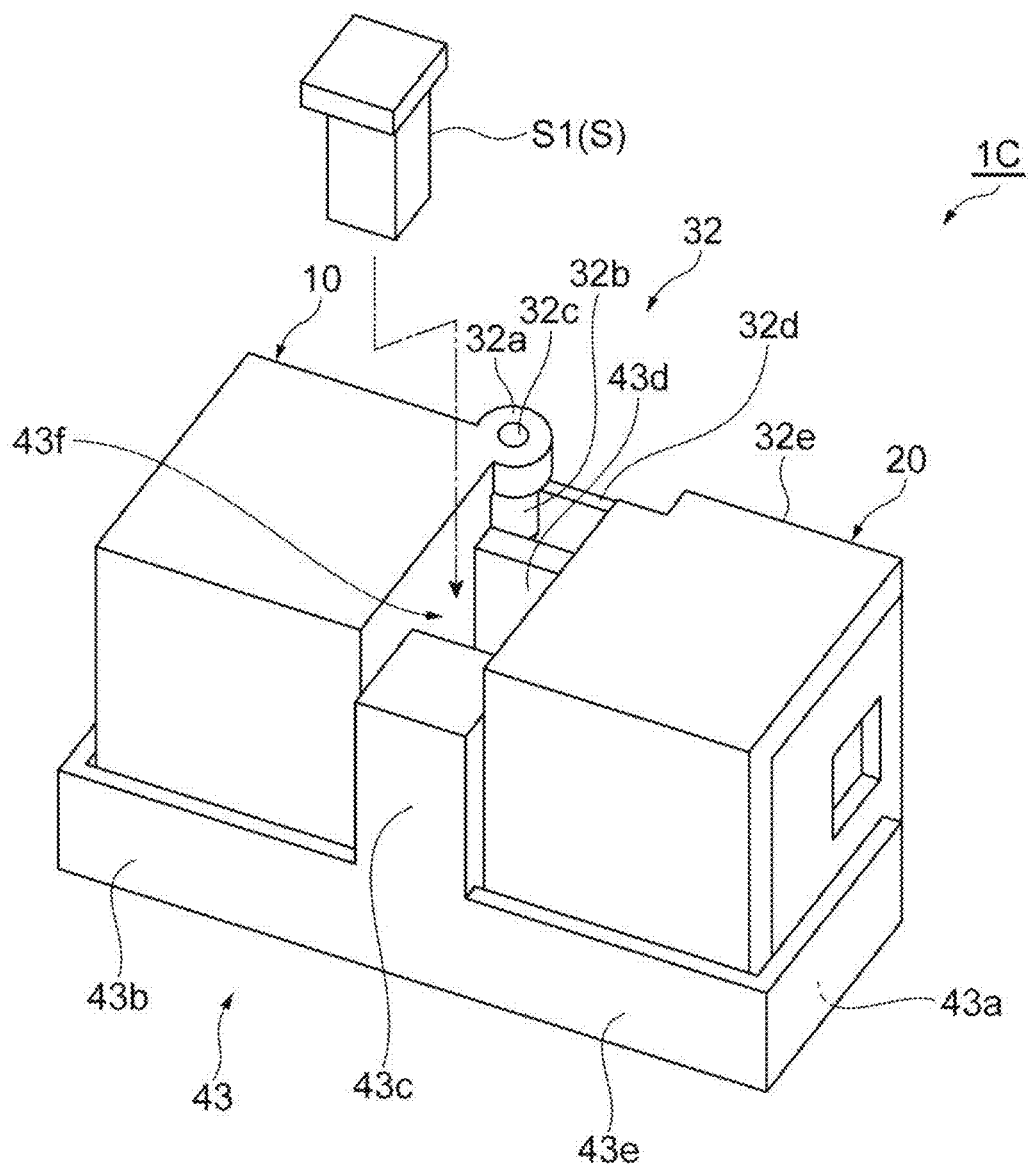
FIG. 17 is a configuration diagram illustrating a spectroscopic measurement device according to a modification.

As illustrated in FIG. 17, the spectroscopic measurement device 1C according to the third embodiment may further include an attachment 43. The attachment 43 makes it easy to hold the light source 11 of the first housing 10 and the spectrometer 21 of the second housing 20 in a state of being disposed in desired relative positions for performing transmitted light measurement. The desired relative position is a position at which the optical axis of the light L1 emitted on the cuvette S1 containing the measurement target S and the optical axis of the measurement light L2 output from the measurement target S are coaxial. The attachment 43 detachably holds the first housing 10, the cuvette S1, and the second housing 20 sequentially in this order. The attachment 43 includes a main body 43*a*, wall portions 43*b* and 43*e*, and column portions 43*c* and 43*d*. The main body 43*a* has a rectangular plate shape. The wall portions 43*b* and 43*e* and the column portions 43*c* and 43*d* are provided upright on the main body 43*a*. The wall portions 43*b* and 43*e* and the column portions 43*c* and 43*d* hold the first housing 10, the cuvette S1 containing the measurement target S, and the second housing 20.

The wall portion 43*b* is formed in an L shape along an edge portion on one side in the longitudinal direction of the main body 43*a* in plan view. Specifically, the wall portion 43*b* includes a portion along one end edge of the main body 43*a* and a portion along one side edge continuous to the one end edge. The wall portion 43*e* is formed in an L shape along the other edge portion on the opposite side to the one side in the longitudinal direction of the main body 43*a* in plan view. Specifically, the wall portion 43*e* has a portion along the other end edge opposite to the one end edge of the main body 43*a*, and a portion along one side edge continuing from the other end edge.

The column portion 43*c* is formed between the wall portions 43*b* and 43*e* in the longitudinal direction of the main body 43*a* so as to be continuous with the wall portions 43*b* and 43*e*. The column portion 43*c* is formed thicker in the short-side direction of the main body 43*a* than the wall portions 43*b* and 43*e*. The column portion 43*d* is provided upright at a predetermined interval in the short-side direction of the main body 43*a* with respect to the column portion 43*c*. This predetermined interval corresponds to the external dimension of the cuvette S1 (length of the cuvette S1 in the short-side direction of the main body 43*a* in a state where the cuvette S1 is held by the attachment 43). Furthermore, the column portion 43*d* is formed such that the width of the main body 43*a* in the longitudinal direction is substantially the same as the width of the column portion 43*c*. This width corresponds to the external dimension of the cuvette S1 (length of the cuvette S1 in the longitudinal direction of the main body 43*a* in a state where the cuvette S1 is held by the attachment 43).

The wall portion 43*b* and the column portions 43*c* and 43*d* define a space to contain the first housing 10 so as to be engaged with the first housing 10. The wall portion 43*e* and the column portions 43*c* and 43*d* define a space to contain the second housing 20 so as to be engaged with the second housing 20. The first housing 10 and the second housing 20 may be detachably secured to at least one of the main body 43*a*, the wall portions 43*b* and 43*e*, and the column portions 43*c* and 43*d* by a screw or the like.

With the above configuration, the attachment 43 holds the first housing 10 such that the first opening 10*a* faces the cuvette S1 side by the wall portion 43*b* and the column portions 43*c* and 43*d*. Furthermore, the attachment 43 holds the second housing 20 such that the second opening 20*a* faces the cuvette S1 side by the wall portion 43*e* and the column portions 43*c* and 43*d*. That is, the attachment 43 holds the first housing 10 and the second housing 20 so that the first opening 10*a* and the second opening 20*a* face each other. In other words, the attachment 43 holds the first housing 10 and the second housing 20 such that the optical axis of the light L1 emitted on the cuvette S1 and the optical axis of the measurement light L2 output from the cuvette S1 are coaxial. Furthermore, the attachment 43 holds the cuvette S1 by the column portions 43*c* and 43*d*.

Note that the column portion 43*c* may include, at its tip, a pressing part for pressing at least one of the first housing 10 and the second housing 20 toward the main body 43*a* side. Specifically, the column portion 43*c* may have an elongated pressing part extending from the tip of the column portion 43*c* to both ends in the longitudinal direction of the main body 43*a* at a position having a height substantially the same as the height of the upper surface of the first housing 10 (the second housing 20) in illustration. In other words, the column portion 43*c* may have a substantially T shape including the pressing part formed at the distal end side as viewed in the short-side direction of the main body 43*a*. In this case, the attachment 43 can firmly hold the first housing and the second housing.

Next, a method of performing transmitted light measurement of the measurement target S contained in the cuvette S by using the spectroscopic measurement device 1C according to the present modification will be described.

As illustrated in FIG. 17, first, the first housing 10 and the second housing 20 are rotated relative to each other by the junction 32 such that the first opening 10*a* and the second opening 20*a* face each other, and together with this, the second housing 20 is slid with respect to the first housing 10 so that the length between the first opening and the second opening becomes equal to the width of the column portions 43*c* and 43*d* in the longitudinal direction of the main body 43*a*. Thereafter, the first housing 10 is disposed between the wall portion 43*b* and the column portions 43*c* and 43*d*, while the second housing 20 is disposed between the wall portion 43*e* and the column portions 43*c* and 43*d*. Next, the cuvette S1 is disposed between the column portions 43*c* and 43*d*. With this arrangement, the optical axis of the light L1 emitted on the measurement target S contained in the cuvette S1 and the optical axis of the measurement light L2 output from the measurement target S are coaxial.

Subsequently, the light L1 is emitted from the light source 11. The emitted light L1 passes through the first opening 10*a* and is directed to the cuvette S1. The measurement light L2 as the transmitted light travels toward the second opening 20*a*, and then is received and measured by the spectrometer 21.

As described above, it is possible to arrange the light source 11 and the spectrometer 21 at desired relative positions and downsize the apparatus also in the spectroscopic measurement device 1C according to the present modification. Moreover, since the spectroscopic measurement device 1C further includes the attachment 43 to detachably hold the first housing 10 and the second housing 20 joined by the junction 32, making it possible to use the attachment 43 to hold the first housing 10 and the second housing 20 positioned in a desired positional relationship by the junction 32.

The spectroscopic measurement device 1C according to the present modification can allow the column portions 43c and 43d of the attachment 43 to function as the position regulator 43f for regulating the position of the cuvette S1, enabling the cuvette S1 to be reliably held by the position regulator 43f.

Other Modifications

Figure 18:
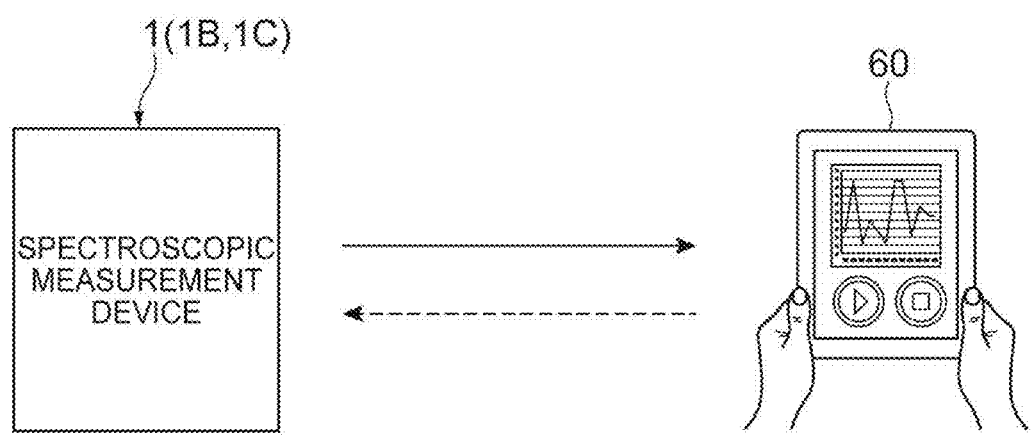
FIG. 18 is a configuration diagram illustrating a spectroscopic measurement device according to a modification.

As illustrated in FIG. 18, in the above embodiment, the spectroscopic measurement device 1 and the mobile information terminal 60 may be configured to be capable of directly communicating without going through a network. In this case, the measurement result of the spectrometer 21 of the spectroscopic measurement device 1 may be directly transmitted wirelessly from the wireless communication unit 22a to the mobile information terminal 60, and then, the measurement result may be processed by the mobile information terminal 60, and the processing result may be displayed on the interface of the mobile information terminal 60. Additionally, in this case, a control signal to control the light source 11 may be directly transmitted from the mobile information terminal 60 to the wireless communication unit 22a by radio. Here, the mobile information terminal 60 functions as a control terminal and a measurement result processing device.

In the above embodiment, one side surface 10b on which the first opening 10a is formed out of the outer surfaces of the first housing 10 may include a rubber layer. Similarly, one side surface 20b on which the second opening 20a is formed out of the outer surfaces of the second housing 20 may include a rubber layer. This can enhance the light shielding property. In addition, since the first housing 10 and the second housing 20 can be abutted against the measurement target S via the rubber layer, the first housing 10 and the second housing 20 can be firmly pressed against the measurement target S, making it possible to strongly hold the measurement target S.

In the first to third embodiments described above, the transmitted light measurement or the reflected light measurement can be replaced by the fluorescence measurement of measuring the fluorescence generated in the measurement target S as the measurement light L2. Specifically, fluorescence measurement may be performed in place of transmitted light measurement in a case where the relative positions of the light source 11 and the spectrometer 21 are such that the optical axis of the light L1 and the optical axis of the measurement light L2 are coaxial. Fluorescence measurement may be performed in place of reflected light measurement in a case where the relative positions of the light source 11 and the spectrometer 21 are such that the optical axis of the light L1 and the optical axis of the measurement light L2 intersect at a predetermined angle.

The spectroscopic measurement device or the spectrometry system according to the above embodiment may include a plurality of types of attachments (for example, all or a part of the attachments 40 to 43). In this case, one of the plurality of types of attachments is selected in accordance with the desired relative positions of the light source 11 and the spectrometer 21 as a desired arrangement in the spectrometry. Spectrometry is performed by using the selected attachment. Note that one aspect of the present invention can also be regarded as a spectrometric method of performing spectrometry using the spectroscopic measurement device or the spectrometry system according to the above embodiment.

INDUSTRIAL APPLICABILITY

The technology makes it possible to provide a spectroscopic measurement device capable of disposing the light source and the spectrometer at desired relative positions and downsizing the device, and a spectrometry system including the spectroscopic measurement device.

REFERENCE SIGNS LIST 1, 1B, 1C Spectroscopic measurement device
10 First housing
10a First opening
11 Light source
22b Light source control unit
20 Second housing
20a Second opening
21 Spectrometer
22a Wireless communication unit (measurement result transmission unit, control signal reception unit)
30, 31, 32 Junction
40, 41, 42, 43 Attachment
40g, 41g, 42g, 43f Position regulator
40h, 41h, 42h First optical path
40i, 41i, 42i Second optical path
50 Data processing server (measurement result processing device)
60 Mobile information terminal (control terminal, measurement result processing device)
100 Spectrometry system
N Network
S Measurement target
S1 Cuvette (container)
L1 Light
L2 Measurement light

The invention claimed is:

1. A spectroscopic measurement device configured to emit light onto a measurement target to measure measurement light output from the measurement target corresponding to the light emission,
the device comprising:
a first housing having a light shielding property and configured to house a light source that emits light and having a first opening through which the light emitted from the light source passes;
a second housing having a light shielding property and having a second opening through which the measurement light passes and configured to house a spectrometer that receives the measurement light that has passed through the second opening; and
a junction configured to join the first housing and the second housing such that relative positions of the first housing and the second housing can be changed.

2. The spectroscopic measurement device according to claim 1, wherein the junction relatively rotatably joins the first housing and the second housing.

3. The spectroscopic measurement device according to claim 1, wherein the junction slidably joins either one of the first housing and the second housing with respect to the other in a direction to allow the first opening and the second opening to come closer to or away from each other.

4. The spectroscopic measurement device according to claim 1, wherein the junction is capable of changing the relative positions to positions where the first opening and the second opening face each other.

5. The spectroscopic measurement device according to claim 1,
wherein the junction is capable of changing the relative positions to a position at which an optical axis of the light to be emitted onto the measurement target and an optical axis of the measurement light output from the measurement target intersect at a predetermined angle.

6. The spectroscopic measurement device according to claim 1, further comprising an attachment configured to detachably hold the first housing and the second housing joined by the junction.

7. The spectroscopic measurement device according to claim 6,
wherein the attachment has a light shielding property, and the attachment internally includes: a first optical path being an optical path of the light emitted onto the measurement target and is continuous with the first opening; and a second optical path being an optical path of the measurement light output from the measurement target and is continuous with the second opening.

8. The spectroscopic measurement device according to claim 6, wherein the attachment has a position regulator configured to regulate a position of the measurement target or a container accommodating the measurement target.

9. A spectrometry system comprising:
the spectroscopic measurement device according to claim 1;
a measurement result transmission unit provided in the spectroscopic measurement device and configured to transmit a measurement result of the spectrometer; and
a measurement result processing device configured to receive the measurement result of the spectrometer from the measurement result transmission unit directly or through a network and perform processing of the measurement result.

10. The spectrometry system according to claim 9, further comprising:
a control terminal configured to generate a control signal for controlling the light source in accordance with operation of an operator and transmit the control signal;
a control signal reception unit provided in the spectroscopic measurement device and configured to receive the control signal from the control terminal directly or through a network; and
a light source control unit provided in the spectroscopic measurement device and configured to control the light source on the basis of the control signal received by the control signal reception unit.

11. The spectroscopic measurement device according to claim 2, further comprising an attachment configured to detachably hold the first housing and the second housing joined by the junction.

12. The spectroscopic measurement device according to claim 3, further comprising an attachment configured to detachably hold the first housing and the second housing joined by the junction.

13. The spectroscopic measurement device according to claim 4, further comprising an attachment configured to detachably hold the first housing and the second housing joined by the junction.

14. The spectroscopic measurement device according to claim 5, further comprising an attachment configured to detachably hold the first housing and the second housing joined by the junction.

15. The spectroscopic measurement device according to claim 7, wherein the attachment has a position regulator configured to regulate a position of the measurement target or a container accommodating the measurement target.

* * * * *